US006872523B1

(12) United States Patent
Iwen et al.

(10) Patent No.: US 6,872,523 B1
(45) Date of Patent: Mar. 29, 2005

(54) MATERIALS AND METHODS FOR MOLECULAR DETECTION OF CLINICALLY RELEVANT PATHOGENIC FUNGAL SPECIES

(75) Inventors: Peter C. Iwen, Omaha, NE (US); Steven H. Hinrichs, Omaha, NE (US); Travis Henry, Omaha, NE (US)

(73) Assignee: The Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 09/580,797

(22) Filed: May 30, 2000

(51) Int. Cl.[7] .......................... C07H 21/04; C12Q 1/68
(52) U.S. Cl. ......................... 435/6; 435/91.1; 435/91.2; 536/23.1; 536/24.32; 536/24.3
(58) Field of Search .......................... 435/6, 91.1, 91.2; 536/23.1, 24.32, 24.3

(56) References Cited

U.S. PATENT DOCUMENTS

| | | | | |
|---|---|---|---|---|
| 5,707,802 A | * | 1/1998 | Sandhu et al. | 435/6 |
| 5,827,656 A | * | 10/1998 | Nelson et al. | 435/6 |
| 5,827,695 A | * | 10/1998 | Beck | 435/6 |
| 5,876,977 A | * | 3/1999 | Wang et al. | 435/91.2 |
| 6,165,720 A | * | 12/2000 | Felgner et al. | 435/6 |

OTHER PUBLICATIONS

Pazoutova. Genbank Accession No. AJ00133, Aug. 1997.*

Peterson. Genbank Accession No. U65306, Jan. 1998.*

De Aguirre et al. Genbank Accession No. U93683, May 1997.*

Nikkuni et al. "Evolutionary relationships amon Aspergillus oryzae and related species based on the sequences of 18S rRNA genes and internal transcribed spacers". J. Gen. Appl. Microbiol. vol. 44, p. 225–230, 1998.*

Borsuk et al. "Evolutionary conservation of the transcribed spacer sequences of the rDAN repeat unit in three species of the genus Aspergillus". Acta Biochimica Polonica. vol. 41, No. 1, pp. 73–77, 1994.*

White et al. "Amplification and direct sequencing of fungal ribosomal RNA genes for phylogenetics". PCR Protocols: A Guide to Methods and Applications. 1990.*

P.C. Iwen et al., "Culture Identification of Histoplasma capsulatum Using the rDNA Internal Transcribed Spacer Regions 1 and 2 as a Molecular Target"; Session No. 185/F. Abstract F–57, May 24, 2000.

David W. Denning, "Therapeutic Outcome in Invasive Aspergillosis"; Clinical Infectious Diseases, 1996: 23:608–15.

Giles J. Gaskell et al., "Analysis of the internal transcribed spacer regions of ribosomal DNA in common airborne allergenic fungi"; Electrophoresis, 1997, 18, 1567–1569.

Takashi Sugita et al., "Identification of Medically Relevant Trichosporon Species Based on Sequences of Internal Transcribed Spacer Regions and Construction of a Database for Trichosporon Identification"; Journal of Clinical Microbiology, Jun. 1999, p. 1985–1993.

Christine Y. Turenne et al., Rapid Identification of Fungi by Using the ITS2 Genetic Region and an Automated Fluorescent Capillary Electrophoresis System; Journal of Clinical Microbiology, Jun. 1999, p. 1846–1851.

Y.C. Chen et al., "Identification of Medically Important Yeasts Using PCR–Based Detection of DNA Sequence Polymorphisms in the Internal Transcribed Spacer 2 Region of the rRNA Genes"; Journal of Clinical Microbiology, Jun. 2000, p. 2302–2310.

Cheryl M. Elie et al, "Rapid Identification of Candida Species with Species–Specific DNA Probes"; Journal of Clinical Microbiology, Nov. 1998, p. 3260–3265.

Peter C. Iwen et al., "Pulmonary Infection Caused by Gymnascella hyalinospora in a Patient with Acute Myelogenous Leukemia"; Journal of Clinical Microbiology, Jan. 2000, p. 375–381.

Travis Henry et al., "Identification of Aspergillus Species Using Internal Transcribed Spacer Regions 1 and 2"; Journal of Clinical Microbiology, Apr. 2000, p. 1510–1515.

Paul C. Iwen, "Pulmonary Aspergillosis Due to Aspergillus terreus: 12–Year Experience . . . view of the Literature"; CID 1998:26 (May), p. 1092–1097.

Daniel J. Sheehan et al., "Current and Emerging Azole Antifungal Agents"; Clinical Microbiology Reviews, Jan. 1999, p. 40–79, vol. 12, No. 1.

Jean–Paul Latge, "Aspergillus fumigatus and Aspergillosis"; Clinical Microbiology Reviews, Apr. 1999, p. 310–350, vol. 12, No. 2.

* cited by examiner

*Primary Examiner*—W. Gary Jones
*Assistant Examiner*—Jeanine Goldberg
(74) *Attorney, Agent, or Firm*—Dann, Dorfman, Herrell and Skillman

(57) ABSTRACT

Materials and methods are provided which rapidly and specifically different between pathogenic and non-pathogenic Aspergillus species in a biological sample.

12 Claims, 1 Drawing Sheet

MATERIALS AND METHODS FOR MOLECULAR DETECTION OF CLINICALLY RELEVANT PATHOGENIC FUNGAL SPECIES

FIELD OF THE INVENTION

This invention relates to the field of molecular biology and to the detection of detrimental fungal species. More specifically, the invention provides materials and methods which facilitate the identification of pathogenic fungal species in infected patients.

BACKGROUND OF THE INVENTION

Several publications are referenced in this application by numerals in parentheses in order to more fully describe the state of the art to which this invention pertains. Full citations for these references are set forth at the end of the specification. The disclosure of each of these publications is incorporated by reference herein.

Fungi are eukaryotic microorganisms that are universally distributed. In nature, fungi play a major role in the decomposition of plant materials. They are also responsible for spoilage of food and in the preparation of beverages and pharmaceuticals. Out of an estimated 100,000 species of fungi described by mycologists, approximately 150 species are recognized as pathogens in humans and animals. The increasing incidence of AIDS and the development of newer treatments for hematologic malignancies and solid organ transplants has led to an increase in the number of immunocompromised patients. These patients have a high risk of developing fungal infections, which, if not rapidly diagnosed and treated, are capable of causing death in a matter of days. The number of antifungal drugs is limited and their toxic side effects on the patient are much higher than that of comparable antibacterial therapy. Therefore, a rapid diagnosis of a fungal infection with administration of appropriate therapy is critical in these patients.

Aspergillus species, for example, are associated with allergic bronchopulmonary disease, mycotic keratitis, otomycosis, nasal sinusitis, and invasive infection. The most severe disease caused by the aspergilli occurs in immunocompromised patients with invasive pulmonary infection followed by rapid dissemination. The frequency of invasive aspergillosis (IA), as well as other invasive mold infections has increased.in recent years due to the expanding number of patients receiving aggressive chemotherapy regimens and immunosuppressive agents (2). The nonspecific symptoms and the lack of rapid diagnostic assays to detect these infections have been major problems in treating patients with invasive disease Early recognition of invasive fungal infection and treatment with appropriate antifungal therapy is key to reducing the mortality associated with disseminated disease (25). The mortality rate for bone marrow transplant patients with pulmonary IA is greater than 70% (5, 15). Due to the typically long time required for identification of a mold using standard culture procedures, most patients with suspected disease are treated empirically with amphotericin B (AmB). Resistance to AmB as well as itraconazole has been reported for some Aspergillus species although the number of isolates studied in each case is limited (14, 16).

Unfortunately, the identification of the aspergilli based on morphologic methods requires adequate growth for evaluation of colony characteristics and microscopic features. A culture time of 5 days or more is generally required for identification of anamorphic forms of Aspergillus. There are more than 180 species in the Aspergillus genus, although three, including *A. flavus, A. fumigatus* and *A. terreus* account for the vast majority of IA infections. *A. nidulans, A. niger* and *A. ustus* are rarely encountered as causes of invasive disease(18).

Various molecular approaches have been used for the detection of Aspergillus from environmental and clinical samples (3, 6, 27). Targets for the genus-level detection of Aspergillus have included the 18S rRNA gene, mitochondrial DNA, the intergenic spacer region, and the internal transcribed spacer (ITS) regions. The ITS regions are located between the 18S and 28S rRNA genes and offer distinct advantages over other molecular targets including increased sensitivity due to the existence of approximately 100 copies per genome. The rRNA gene for 5.8S RNA separates the two ITS regions. The sequence variation of ITS regions has led to their use in phylogenetic studies of many different organisms (9, 26).

It would be highly advantageous if means were available to differentiate and efficiently identify clinically relevant pathogenic fungi. It is an object of the present invention to provide compositions, methods and kits to accomplish this goal.

SUMMARY OF THE INVENTION

Numerous fungi, once thought to be nonpathogens, have emerged as causes of human disease (31,32,34). The identification of these unusual fungal pathogens is difficult, frequently requiring the expertise of a fungal reference laboratory. The uniqueness of the nucleic acid sequence of the ITS regions allows for the identification of these novel pathogens (30,31,32,34).

In accordance with the present invention, materials and methods are provided which facilitate the differentiation and identification of clinically relevant pathogenic fungal species. In one aspect of the invention, a universal primer set having SEQ ID NOS: 1 and 2 suitable for amplifying ITS amplicons from a wide variety of pathogenic fungal species is provided.

In a preferred embodiment of the invention, methods are disclosed for identifying pathogenic fungal species by virtue of species specific differences in the ITS regions amplified using the universal primer set of the invention. The method comprises determining whether one or more fungal species selected from the group of fungal species consisting of *Aspergillus ustus, Aspergillus terreus, Aspergillus niger, Aspergillus:fumigatus, Aspergillus flavus, Pseudallescheria boydii, Fusarium solani, Fusarium oxysporum, Fusarium monilliformes*, Penicillium spp., *Malassezia furfur*, Malbarnchia spp., *Cylindrocarpon lichenicola, Cladophialophora bantiana*, Arthrogrothilus spp., *Gymnascella hyalinaspora, Cylindrocarpon destructans, Sporothrix schenkii, Blastomyces dermatitides, Penicillium marnefeii, Histoplasma duboisii, Histoplasma capsulatum, Coccidiodes immitis, Czyptococcus neoformans, Issatchenkia orientalis, Candida albicans, Candida tropicalis, Candida lusitaniae, Candida glabrata*, and *Candida parapsilosis*, is present in a biological sample. The steps of the method include a) extracting nucleic acid material from fungi contained in the sample; b) adding two known oligonucledtide primers, one of the primers being (SEQ ID NO:1) and the other primer being (SEQ ID NO:2), the primers bracketing a hypervariable region on the rRNA present in the fungal species of the group; c) amplifying the sequence between the primers; and d) using one or more detectably labeled probes directed to a portion of the hypervariable region bracketed by the primers, each of the labeled probes being specific for one of the fungal species from said group. In a preferred embodiment the target ITS sequences are amplified by polymerase chain reaction. The one or more probes recited in the method are selected from the group consisting of (SEQ ID NO:3), (SEQ ID NO:4), (SEQ ID NO:5), (SEQ ID NO:6), (SEQ ID NO:7), (SEQ ID NO:8), (SEQ ID NO:9), (SEQ ID NO:10), (SEQ ID NO:11), (SEQ ID NO:12), (SEQ ID NO;13), (SEQ ID NO:14), (SEQ ID NO:15), (SEQ ID NO:16), (SEQ ID NO:17), (SEQ ID NO:18), (SEQ ID NO:19), (SEQ ID NO:20), (SEQ ID NO:21), (SEQ ID NO:22) and (SEQ ID NO:23), (SEQ ID NO: 24),(SEQ ID NO:25),(SEQ ID NO:26),(SEQ ID NO:27),(SEQ ID NO:28), (SEQ:ID NO:29),(SEQ ID NO:30), and (SEQ ID NO:31), (SEQ ID NO:32), (SEQ ID NO:33), each having a characteristic ITS sequence indicating fungal species of origin. In a further embodiment of the method, a plurality of probes are used in its step (d each being connected to (a) a different signal moiety or (b) a moiety which allows separation of said probes.

The following fungal specific oligonucleotide sequences for use as probes in the methods of the invention are also provided herein. An oligonucleotide sequence specific for Penicillium.spp., having the nucleotide sequence of (SEQ ID NO:25) or the complement thereof; an oligonucleotide sequence specific for Malbranchia spp., having the sequence of (SEQ ID NO:26) or the complement thereof; an oligonucleotide sequence specific for Arthorgrothilus spp., having the sequence of (SEQ ID NO:27) or the complement thereof; an oligonucleotide sequence specific for *Cylindrocarpon destructans*, having the sequence of (SEQ ID NO:28) or the complement thereof; an oligonucleotide sequence specific for *Sporothrix schenkii*, having the sequence of (SEQ ID NO:29) or the complement thereof; an oligonucleotide sequence specific for *Penicillium marnefeii*, having the sequence of (SEQ ID NO:30) or the complement thereof; an oligonucleotide sequence specific for *Coccidiodes immitis*, having the sequence of (SEQ ID NO:31) or the complement thereof; an oligonucleotide sequence specific for *Candida tropicalis*, having the sequence (SEQ ID NO:32) or the complement thereof; an oligonucleotide sequence specific for *Candida parapsilosis*, having the sequence of (SEQ ID NO:33) or the complement thereof.

Also within the scope of the present invention, are kits for identifying pathogenic fungal species in a biological sample. The kits comprise 1) a universal primer set, having the sequence of SEQ ID NO: 1 and SEQ ID NO: 2; 2) lysis buffer suitable for lysing fungus in the biological sample, such that DNA is released from the fungus upon exposure to said buffer; 3) a polymerase enzyme suitable for use in PCR 4) means for contacting said released DNA with a primer set having the sequence of SEQ ID NO: 1 and NO: 2 under conditions where amplification of pathogenicity-associated ITS sequences occurs, if said pathogenic fungus is present in said sample; and 5) means for detecting said amplified sequence, if present. In a further embodiment, the kit of the invention, contains sequences having SEQ ID NOS: 3–33 for comparing the amplified fungal ITS sequence thereby identifying said pathogenic fungus if present.

With reference to nucleic acids used in the invention, the term "isolated nucleic acids" is sometimes employed. This term, when applied to DNA, refers to a DNA molecule that is separated from sequences with which it is immediately-.contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a procaryotic or eucaryotic cell. An "isolated nucleic acid molecule" may also comprise a cDNA molecule. An isolated nucleic acid molecule inserted into a vector is also sometimes referred to herein as a "recombinant" nucleic acid molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

The term "substantially pure" refers to a preparation comprising at least 50–60% by weight the compound of interest (e.g., nucleic acid, oligonucleotide, protein, etc.). More preferably, the preparation comprises at least 75% by weight, and most preferably 90–99% by weight, the compound of interest. Purity is measured by methods appropriate for the compound of interest (e.g. chromatographic methods, agarose or polyacrylamide gel electrophoresis, HPLC analysis, and the like).

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Samnbrook et al., *Molecular Cloning*, Cold Spring Harbor Laboratory (1989) (29):

$$T_m=81.5°\ C.+16.6\ \mathrm{Log}[Na+]+0.41(\%\ G+C)-0.63(\%\ \mathrm{formamide})-600/\#bp\ \mathrm{in\ duplex}$$

As an illustration of the above formula, using [Na+]=[0.368] and 50% formamide, with GC content of 42% and an average probe size of 200 bases, the $T_m$ is 57° C. The $T_m$ of a DNA duplex decreases by 1–1.5° C. with every 1% decrease in homology. Thus, targets with greater than about 75% sequence identity would be observed using a hybridization temperature of 42° C.

The term "oligonucleotide," as used herein refers to primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15–25 or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The phrase "solid matrix" as used herein includes, without limitation, filter paper, multiwell dishes, microchips, derivatized magnetic particles and the like.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield an primer extension product. The primer may vary in length depending on the particular conditions and requirement of the application. For example, in diagnostic applications, the oligonucleotide primer is typically 15–25 or more nucleotides in length. The primer must be of sufficient complementarity to the desired template to to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact a complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

DETAILED DESCRIPTION OF THE INVENTION

Figure 1:
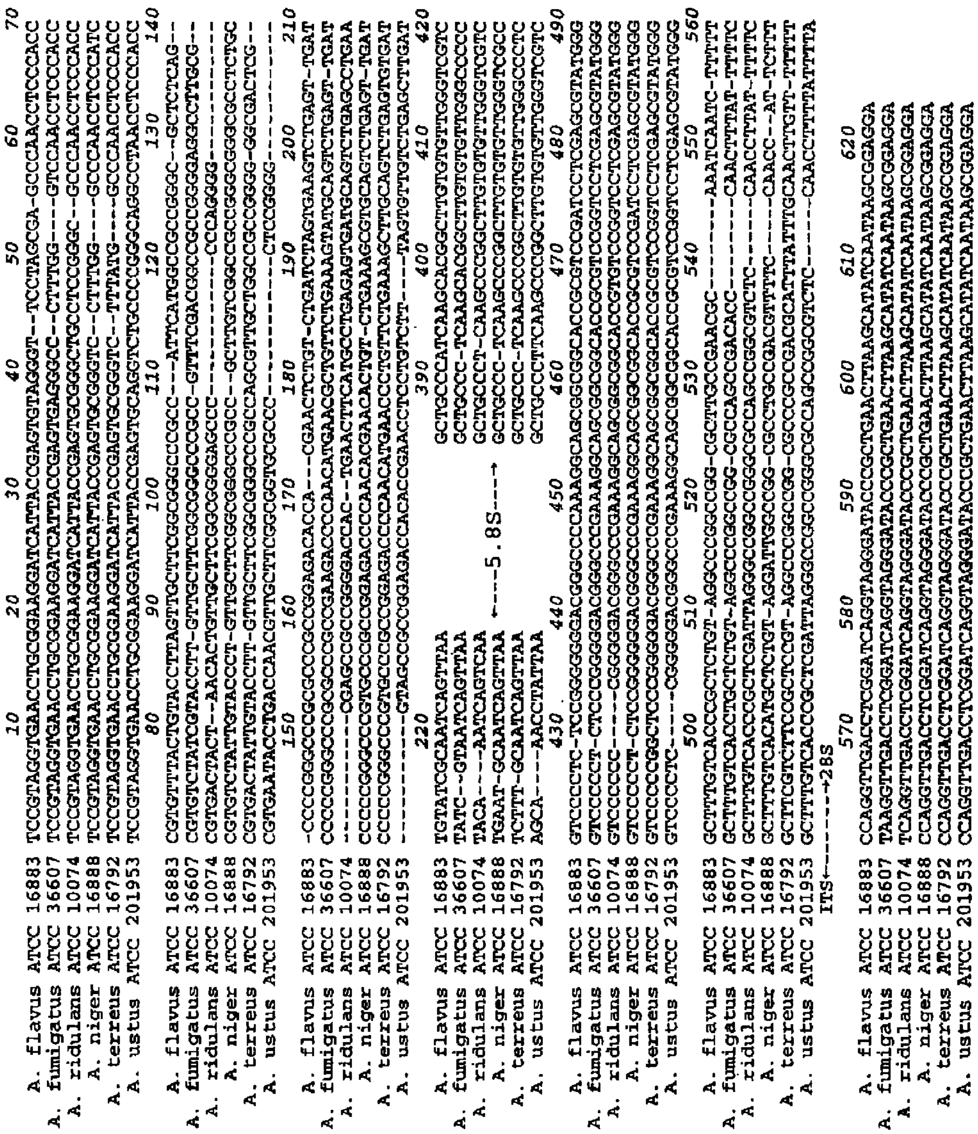
FIG. 1 shows the nucleotide sequence alignment of *A. flavus* (ATCC 16883), *A. fumigatus* (ATCC 36607), *A. nidulans* (ATCC 10074), *A. niger* (ATCC 16888), *A. terreus* (ATCC 16792), and *A. ustus* (ATCC 301953). The alignment consists of the 3' end of the 18s ribosomal RNA (rRNA) gene, the complete ITS region, the complete ITS 2 region, and the 5' end of the 28S rRNA gene. The highly conserved 5.8S rRNA gene sequence has been omitted.

Each of the cells of all life forms, except viruses, contain ribosomes and therefore the gene for ribosomal RNA. A ribosome contains three separate single-stranded RNA molecules, namely, a large molecule, a medium sized molecule, and a small molecule. The two larger rRNA molecules vary in size in different organisms.

Ribosomal RNA is a direct gene product and is coded for by the rRNA gene. This DNA sequence is used as a template to synthesize rRNA molecules. A separate gene exists for each of the ribosomal RNA subunits. Multiple rRNA genes exist in most organisms and many higher organisms contain both nuclear and mitochondrial rRNA genes. Plants and certain other organisms contain nuclear, mitochondrial and chloroplast rRNA genes. The rRNA gene and gene product have been well characterized in certain species. Hybridization of rRNA and ribosomal genes in genetic analysis and evolution and taxonomic classification of organisms and ribosomal gene sequences has been described. Genetic analysis may include, for example, the determination of the numbers of rRNA genes in various organisms; the determination of the similarity between the multiple rRNA genes which are present in cells; determination of the rate and extent of synthesis of rRNA in cells and the factors which control them.

In accordance with the present invention, specific sequences have been selected which allow for the identification of clinically relevant pathogenic fungal species unambiguously. The selection of specific sequences is based on differences in the internal transcribed spacer molecules between rRNA genes. These sequences may be used to advantage in methods routinely practiced in the laboratory setting.

The present invention is directed to compositions and methods utilizing sequences from phylogenetically informative segments of rRNA genes from a large variety of fungal isolates.

I. Preparation of Numcleic Acid Molecules and Primers which Differentiate among Fungal Species

A. NUCLEIC ACID MOLECULES

Extraction of DNA from fungi was performed following the needle inoculation of 50 ml of Sabouraud dextrose (SAB) broth (Difco Laboratories: Detroit, MICH.) with conidia from a 7 day culture from SAB agar and incubation for 72 h at 30° C. The hyphae were recovered on a 0.45 μm filter and washed with sterile saline. Aliquots of the fungal hyphae were stored frozen at −70 ° C. until use. Prior to lysis, the hyphae were thawed and suspended in 400 μl of DNA extraction buffer (1 mM EDTA, pH 8.0; 1% sodium dodecyl sulfate, 10 mM Tris-HCL, pH 7.6; 100 mM NaCl, 2% Triton X100) as described by Van Burik et al. (24). Microcentrifuge tubes (1.5 ml.) containing hyphae and buffer were sonicated in a water bath (Branson, Model 2210) for 15 m followed by heating at 100° C. for 5 m. Following lysis, DNA was purified using the QIAmp blood kit (Qiagen Inc, Valencia, Calif.) and protocols for crude cell lysates as supplied by the manufacturer. Following extraction, the purified DNA was stored at 4° C. until tested. Extraction of DNA from blood, paraffinized tissue or other clinical material is performed by adding a small sample of specimen to the fungal DNA extraction buffer and following the procedure as outlined above.

Primer Preparation and Sequence Composition

Nucleic acid molecules encoding the differentiating oligonucleotides of the invention may be prepared by synthesis from appropriate nucleotide triphosphates, a method utilizing protocols well known in the art. The availability of nucleotide sequence information, such as primers having the sequence of SEQ ID NO:1 or SEQ ID NO:2 enables preparation of an isolated nucleic acid molecule of the invention by oligonucleotide synthesis. Synthetic oligonucleotides may be prepared by the phosphoramidite method employed in the Applied Biosystems 38A DNA Synthesizer or similar devices. The resultant primers may be used according to methods known in the art, such as he polymerase chair reation (PCR) method.

Informative ITS sequences from 31 different fungal isolates are provided herein as SEQ ID NOS: 3–33. See Addendum 1. Accordingly, specific probes may be developed for identifying the specific fungi.

In accordance with the present invention, nucleic acids primers having the appropriate level of sequence homology with the sequences provided herein may be identified by using hybridization and washing conditions of appropriate stringency. For example, hybridizations may be performed, according to the method of Sambrook et al.,(1989, supra), using a hybridization solution comprising: 5×SSC, 5×Denhardt's reagent, 1.0% SDS, 100 $\mu$g/ml denatured, fragmented salmon sperm DNA, 0.05% sodium pyrophosphate and up to 50% formamide. Hybridization is carried out at 37–42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 1×SSC and 1% SDS; (4) 2 hours at 42–65 ° C. in 1×SSC and 1% SDS, changing the solution every 30 minutes.

The nucleic acid molecules of the invention include CDNA, genomic DNA, RNA, and fragments thereof which may be single- or double-stranded. Thus, this invention provides oligonucleotides having sequences capable of hybridizing with at least one sequence of a nucleic acid molecule of the present invention, such as selected segments of the sequences provided herein. Also contemplated in the scope of the present invention are oligonucleotide probes which specifically hybridize with the DNA from pathogenic species of fungus under high stringency conditions. Primers capable of specifically amplifying the ITS segments of fungal rDNA encoding nucleic acids described herein are also contemplated to be within the scope of the present invention. As mentioned previously, such oligonucleotides are useful as primers for detecting, isolating and amplifying sequences associated with pathogenic fungus. SEQ ID NOS: 1 and 2 are a suitable universal primer set for this purpose.

It will be appreciated by persons skilled in the art that variants (e.g., allelic variants) of the ITS sequences exist in the fungus population, and must be taken into account when designing and/or utilizing oligonucleotides of the invention. Accordingly, it is within the scope of the present invention to encompass such variants, with respect to the ITS sequences disclosed herein or the oligonucleotides targeted to specific locations on the respective genes or RNA transcripts. Accordingly, the term "natural allelic variants" is used herein to refer to various specific nucleotide sequences of the invention and variants thereof that would occur in a population. The occurrence of genetic polymorphisms which give rise to minor base changes in a DNA molecule are known to those of ordinary skill in the art. Additionally, the term "substantially complementary" refers to oligonucleotide sequences that may not be perfectly matched to a target sequence, but such mismatches do not materially affect the ability of the oligonucleotide to hybridize with its target sequence under the conditions described.

Identification of Fungal Species by Sequence Analysis and/or Probe Hybridization Currently, the most direct method for the identification of fungi is DNA sequence analysis however the methodology is also labor intensive and expensive. It is in usually not practical to sequence all potentially relevant regions of every experimental sample. Other exemplary approaches for recognizing species of fungi based on nucleic acid differences include:

a) comparing the sequence of nucleic acid in the sample with nucleic acid sequences from the non-pathogenic and pathogenic species of fungus to determine which species is responsible for infection in the patient; or b) using DNA restriction mapping to compare the restriction pattern produced when a restriction enzyme cuts a sample of nucleic acid from the sample as compared with the restriction pattern obtained from pathogenic and non-pathogenic species of fungus, or, c) using a specific binding member capable of binding to a either the pathogenic nucleic acid sequence, the specific binding member comprising nucleic acids which distinguish between fungal species based on hybridization specificities, or substances comprising an antibody domain with specificity for a pathogenic or non-pathogenic fungal nucleic acid sequence, the specific binding member being labeled so that binding of the specific binding member to its binding partner is detectable; or d) in situ hybridization between fungal DNA from permeabilized tissue sections and fluorescent molecular probes specific for pathogenic fungal species under investigation; or e) using PCR involving one or more primers based pathogenic fungal gene sequences to screen for the presence of the pathogenic species in a sample.

A "specific binding pair" comprises a specific binding member (sbm) and a binding partner (bp) which have a particular specificity for each other and which under normal conditions bind to each other in preference to other molecules. Examples of specific binding pairs are antigens and antibodies, ligands and receptors and complementary nucleotide sequences. The skilled person is aware of many other examples and they do not need to be listed here. Further, the term "specific binding pair" is also applicable where either or both of the specific binding member and the binding partner comprise a part of a large molecule. In embodiments in which the specific binding pair are nucleic acid sequences, they will be of a length to hybridize to each other under conditions of the assay, preferably greater than 10 nucleotides long, more preferably greater than 15 or 20 nucleotides long.

In most embodiments for screening for the presence of pathogenic fungus the nucleic acid associated with the pathogenic phenotype in the sample will initially be amplified, e.g. using PCR, to increase the amount of the analyte as compared to other sequences present in the sample. This facilitates target sequences detection with a high degree of sensitivity if such sequences are present in the sample. This initial step may be avoided by using highly sensitive array techniques that are becoming increasingly important in the art.

The identification of the specific nucleic acid associated with fungal pathogenicity paves the way for aspects of the present invention to provide the use of materials and methods, such as are disclosed and discussed above, for rapid detection of the presence or absence in a test sample of the fungal pathogen and to identify the fungus to species.

The invention allows for planning of appropriate quarantine and/or prophylactic measures and permits rapid determination of diagnosis and treatment of infected patients.

The following examples are provided to illustrate embodiments of the invention. They are not intended to limit the invention in any way.

EXAMPLE I

Identification of Aspergillus Species using Internal Transcribed Spacer Regions 1 and 2

The following protocols are provided to facilitate the practice of the present invention (taken from a modification of Henry et al. [30]).

Cultures for Analysis

Referenced cultures of Aspergillus species obtained from the American Type Culture Collection (ATCC) included *Aspergillus flavus* ATCC 16883, *A. fumigatus* ATCC 36607, *A. nidulans* ATCC 10074, *A. niger* ATCC 16888, and *A. terreus* ATCC 16792. *A. ustus* was obtained from the University of Alberta Microfungus Collection and Herbarium (UAMH 9479). Isolates of Aspergillus species from cases of IA were obtained from patient samples catalogued at the University of Nebraska Medical Center (UNMC) and inventoried in the Invasive Molds Infection database. Morphologic identification of clinical isolates to the species level was accomplished using established procedures including microscopic and macroscopic characteristics. Additional fungal species selected for sequence comparison with Aspergillus reference strains are *Ajellomyces capsulatus, Ajellomyces dermatitidis, Candida albicans, Cladophialophora bantiana, Cryptococcus neoformans, Cylindrocarpon lichenicola, Fusarium oxysporum, Fusarium solanii*, Fusarium spp., *Gymnascella hyalinospora, Penicillium capsulatum, Penicillium glabrum, Penicillium marnefeii, Phialophora verrucosa, Pseudallescheria boydii*, and *Saccharomyces cerevisiae.*

Culture Preparation and DNA Extraction.

Extraction of DNA from fungi was performed following the needle inoculation of 50 ml of Sabouraud dextrose (SAB) broth (Difco Laboratories: Detroit, Mich.) with conidia from a 7 day culture from SAB agar and incubation for 72 h at 30° C. The hyphae were recovered on a 0.45 $\mu$m filter and washed with sterile saline. Aliquots of the fungal hyphae were stored frozen at −70° C. until use. Prior to lysis, the hyphae were thawed and suspended in 400 $\mu$l of DNA extraction buffer (1 mM EDTA, pH 8.0; 1% sodium dodecyl sulfate, 10 mM Tris-HCL, pH 7.6; 100 mM NaCl, 2% Triton X100) as described by Van Burik et al. (24). Microcentrifuge tubes (1.5 ml.) containing hyphae and buffer were sonicated in a water bath (Branson, Model 2210) for 15 m followed by heating at 100° C. for 5 m. Following lysis, DNA was purified using the QIAmp blood kit (Qiagen Inc, Valencia, Calif.) and protocols for crude cell lysates as supplied by the manufacturer. Following extraction, the purified DNA was stored at 4° C. until tested.

Primers

Modifications of the original primers as stated by Henry et al were made to optimize the amplification procedure (30). The modified 5' primer is 5'GGA AGT AAA AGT CGT AAC AAG G 3' (SEQ ID NO: 1) and the modified 3' primer is 5' GTA TCC CTA CCT GAT CCG AGG 3' (SEQ ID NO: 2). These primers make use of conserved regions of the 18S (SEQ ID NO: 1) and the 28S (SEQ ID NO:2) rRNA genes to amplify the intervening 5.8S gene and the ITS 1 and ITS 2 non-coding regions. Primers were synthesized by the UNMC /Eppley Molecular Biology Core Laboratory.

PCR Amplification

The PCR assay was performed with 5 $\mu$l of test sample in a total reaction volume of 50 $\mu$l consisting of PCR Buffer (20 mM Tris-HCl (pH 8.4) and 50 mM KCl); 0.1 mM (each) dATP, dGTP, dCTP, and dTTP; 1.5 mM $MgCl_2$; 0.3 $\mu$M (each) primer; and 1.5 U of platinum Taq DNA polymerase high fidelity (GibcoBRL, Life Technologies, Gaithersburg, Md.). Forty cycles of amplification were performed in a Stratagene Robocycler Model 96 thermocycler after initial denaturation of DNA at 95° C. for 4.5 m. Each cycle consisted of a denaturation step at 95° C. for 30 s, and annealing step at 50° C. for 30 s, and extension step at 72° C. for 1 m, with a final extension at 72° C. for 3 m following the last cycle. After amplification, the products were stored at 4° C. until used.

Cloning of PCR Products

Amplicons were separated by agarose gel electrophoresis, purified and ligated into the pCR 2.1 plasmid vector using the Invitrogen Original TA Cloning Kit (Invitrogen, San Diego,. Calif.). Competent INV F' One Shot cells were transformed using standard protocols. Colonies were isolated and purified with a Qiagen mini-prep spin kit according to the manufacturer's protocols. An aliquot of purified plasmid was digested with EcoRI endonuclease (New England Biolabs, Beverly, Mass.) and screened by agarose gel electrophoresis for the presence of a 300-bp doublet corresponding to the presence of an EcoRI cleavage site, GAATTC, within the 5.8S sequence. Selected plasmids were submitted to the Eppley Molecular Biology Core Laboratory for automated dye termination sequencing.

DNA Sequencing

DNA sequencing was performed at the Eppley Molecular Biology Core Laboratory on a Perkin Elmer/ABI Model 373 DNA sequencer with protocols supplied by the manufacturer. For sequencing of cloned fragments, both strands of the plasmid containing fungal insert were sequenced with universal M13 forward and reverse sequencing primers. For direct sequencing of non-cloned amplicons, PCR products were directly sequenced using the SEQ ID NO: 1 and the SEQ ID NO: 2 PCR primers. The resultant nucleotide sequences were aligned with the Macvector sequence analysis software Version 6.5 (Oxford Molecular Group, Inc., Campbell, Calif.) alignment application.

GenBank Accession Numbers

The ITS 1-5.8S-ITS 2 rRNA gene complex sequences of referenced Aspergillus species not previously available within the National Center for Biotechnology Information (NCBI) GenBank or European Molecular Biology Laboratory (EMBL) databases were submitted to GenBank. The assigned sequence accession numbers are *A. flavus* (ATCC 16883) as AF138287 (SEQ ID NO:8), *A. fumigatus* (ATCC 36607) as AF138288 (SEQ ID NO: 7), *A. niger* (ATCC 16888) AF138904, *A. terreus* (ATCC 16792) AF138290, and *A. ustus* (ATCC 201953) AF157507. *A. nidulans* (ATCC 10074) AF138289 was accepted into GenBank as *Emericella nidulans*. Sequences from other fungal species also deposited into GenBank are *Ajellomyces capsulatus* AF038353, *Candida albicans* AF217609, *Cladophialophora bantiana* AF131079, *Cryptococcus neoformans*

AF162916, *Cylindrocarpon lichenicola* AF133845, *Gymnascella hyalinospora* AF129854, and *Pseudallescheria boydii* AF181558.

Sequence Analyslis

Sequence comparisons of referenced strains and clinical isolates were made using MacVector 6.5 software (Oxford Molecular Group, Inc.) and the Clustal W alignment algorithm. Intra-species sequence similarity and variation for isolates was determined by the Macvector software and visually confirmed using pairwise nucleotide alignments. Sequences from referenced isolates were aligned to complete or partial ITS sequences available in GenBank after submission of sequence data from this study. Comparison of sequences from referenced isolates, clinical isolates and GenBank sequences was performed using a non-gapped, advanced BLAST search (1). The similarities of the sequences were determined with the expectation frequency minimized to 0.0001. Sequences were not filtered for low complexity.

Clinical Isolate Identification Study

Eleven isolates of various Aspergillus species previously identified by the UNMC Mycology Laboratory were selected by one of us (PI) and innoculated onto Sabouraud dextrose agar and incubated at 30° C. for 24 hours. Isolates included 3 *A. fumigatus,* 2 *A. flavus,* 1 *A. ustus,* 2 *A. terreus,* 2 *A. niger*, and 1 *A. nidulans*. The plates were coded and the presented for processing by a second person (TH). An approximate 2 $mm^3$ section of the agar at the site of innoculation was taken for DNA extraction and amplification. The amplicons were purified using the Qiagen PCR Purification Kit (Qiagen Inc.) and sequenced directly. Sequence analysis of in Aspergillus specimens was performed using an advanced, non-gapped BLAST search with expectation frequency set to 0.0001 and no filtering for low complexity. The search was performed following the deposition and acceptance of sequences from referenced isolates into GenBank. Species identification was determined from the highest bit score of the species listed from the BLAST search. The amount of time from submission of the culture plates to identification was determined.

Results

Analysis of the ITS Regions

Amplification of the ITS 1-5.8S-ITS 2 regions from the six clinically relevant Aspergillus strains generated PCR products ranging in size from 555 to 603 bp (Table 1).

TABLE 1

Aspergillus species PCR products.

| Aspergillus species | Source | Size (bp)[a] |
|---|---|---|
| *A. flavus* | ATCC 16883 | 585 |
| *A. flavus* | clinical isolate | 585 |
| *A. fumigatus* | ATCC 36607 | 586 |
| *A. fumigatus* | clinical isolate | 588 |
| *A. nidulans* | ATCC 10074 | 555 |
| *A. nidulans* | clinical isolate | 559 |
| *A. niger* | ATCC 16888 | 589 |
| *A. niger* | clinical isolate | 589 |
| *A. terreus* | ATCC 16792 | 599 |
| *A. terreus* | clinical isolate | 603 |
| *A. ustus* | UAMH 9479 | 560 |
| *A. ustus* | clinical isolate[b] | 560 |

Abbreviations: ATCC, American Type Culture Collection; UAMH, University of Alberta Microfungus Collection and Herbarium.
[a]Includes the complete ITS 1, 5.8S, ITS 2 regions and portions of the 18S (54 bp) and 28S (25 bp) rRNA genes.
[b]Deposited into the American Type Culture Collection as ATCC 201953.

Sequencing was first performed on cloned amplicons and then repeated using direct sequencing of PCR products with comparisons made between results from both methods. Although a Taq polymerase with proofreading capability was used in generation of amplicons, an examination was made for potential variation in sequence due to random base changes introduced by the amplification process. Two clones from each reference strain for each species were sequenced. The sequence of cloned PCR products varied no more than 2 nucleotides from the sequence of amplicons directly sequenced. Minimal differences in amplicon length were seen between referenced and clinical strains of the same species.

Alignment of contiguous fungal sequences demonstrated that both single nucleotide differencesand short lengths of sequence diversity due to insertions or deletions existed in the ITS 1-5.8S-ITS 2 regions among the pathogenic Aspergillus species (FIG. 1). The ITS 1 region displayed more inter-species variation than the ITS 2 region, with approximately four separate variable regions. ITS 2 contained two variable regions ranging from 6 to 10 bp in length. A matrix analysis of the sequence similarity between ITS 1 and 2 sequences of the referenced Aspergillus species is depicted in Table 2. The greatest similarity among pathogenic species existed between *A. fumigatus* and *A. niger* with 52 nucleotide base differences (91.7% similarity) whereas *A. ustus* showed the greatest diversity when compared with *A. terreus*, with differences at 128 nucleotide positions (79.3% similarity).

TABLE 2

Matrix of ITS 1-5.8S-ITS 2 similarities for referenced Aspergillus species.

| | *A. flavus* ATCC 16883 | *A. fumigatus* ATCC 36607 | *A. nidulans* ATCC 10074 | *A. niger* ATCC 1688 | *A. terreus* ATCC 16792 | *A. ustus* ATCC201953 |
|---|---|---|---|---|---|---|
| *A. flavus* ATCC 16883 | | | | | | |
| *A. fumigatus* ATCC 36607 | 87.6 | | | | | |
| *A. nidulans* ATCC 10074 | 81.5 | 84.3 | | | | |

TABLE 2-continued

| Matrix of ITS 1-5.8S-ITS 2 similarities for referenced Aspergillus species. | | | | | | |
|---|---|---|---|---|---|---|
| | *A. flavus* ATCC 16883 | *A. fumigatus* ATCC 36607 | *A. nidulans* ATCC 10074 | *A. niger* ATCC 1688 | *A. terreus* ATCC 16792 | *A. ustus* ATCC201953 |
| *A. niger* ATCC 16886 | 89.6 | 91.7 | 84.0 | | | |
| *A. terreus* ATCC 16792 | 87.0 | 91.1 | 83.0 | 90.6 | | |
| *A. ustus* ATCC 201953 | 82.7 | 80.7 | 91.4 | 80.5 | 79.3 | |

Aspergillus ITS sequences generated in our laboratory from ATCC strains were compared with all Aspergillus sequences available in GenBank following the deposition of sequences listed in Table 3. For *A. flavus, A. fumigatus*, or *A. terreus*, the inter-species sequence similarity with all Aspergillus GenBank sequences (referenced and non-referenced) was found to be less than 99%. Sequence similarity of 99% was observed between *A. nidulans* (accepted into GenBank as *Emericella nidulans*) and *Emericella quadrilineata*. Sequence similarity of 99% was also found among species within the *A. niger* aggregate including *A. phoenicis* and *A. tubigensis*.

TABLE 3

| Species and accession number | ITS1 | ITS 2 | ITS1-5.8S- ITS 2 | % similarity |
|---|---|---|---|---|
| *Aspergillus flavus* | | | | |
| ATCC 16883 | | | | |
| IMI 210 | 0 | 1 | 1 | 99.8 |
| AB008414 | 0 | 1 | 1 | 99.8 |
| AB008415 | 0 | 2 | 2 | 99.7 |
| AB008416 | 0 | 0 | 0 | 100.0 |
| AF027863 | 0 | 0 | 0 | 100.0 |
| AF078893 | 0 | 1 | 1 | 99.8 |
| AF078894 | 0 | 0 | 0 | 100.0 |
| L76747 | 4 | 0 | 4 | 99.3 |
| *Aspergillus fumigatus* | | | | |
| ATCC 36607 | | | | |
| IMI 196 | 2 | 2 | 5 | 99.2 |
| AF078889 | 2 | 0 | 2 | 99.7 |
| AF078890 | 1 | 0 | 1 | 99.8 |
| AF078891 | 1 | 0 | 1 | 99.8 |
| AF078892 | 1 | 0 | 1 | 99.8 |
| *Aspergillus nidulans* | | | | |
| ATCC 10074 | | | | |
| IMI 231 | 2 | 2 | 4 | 99.3 |
| L76746 | 0 | 0 | 0 | 100.0 |
| U03521 | NA | 2 | 2 | 99.6 |
| *Aspergillus niger* | | | | |
| ATCC 16888 | | | | |
| IMI 026 | 0 | 0 | 0 | 100.0 |
| AF078895 | 0 | 0 | 0 | 100.0 |
| AJ223852 | 4 | 1 | 5 | 99.2 |
| L76748 | 0 | 0 | 0 | 100.0 |
| U65306 | 0 | 0 | 0 | 100.0 |
| *Aspergillus terreus* | | | | |
| ATCC 16792 | | | | |
| IMI 203 | 4 | 0 | 4 | 99.3 |
| AF078896 | 0 | 0 | 0 | 100.0 |

TABLE 3-continued

| Species and accession number | ITS1 | ITS 2 | ITS1-5.8S- ITS 2 | % similarity |
|---|---|---|---|---|
| AF078897 | 0 | 0 | 0 | 100.0 |
| AJ001334 | 0 | 0 | 0 | 100.0 |
| AJ001335 | 0 | 0 | 0 | 100.0 |
| AJ001338 | 0 | 0 | 0 | 100.0 |
| AJ001368 | 0 | 1 | 1 | 99.8 |
| L76774 | 0 | 0 | 0 | 100.0 |
| U93684 | 0 | 3 | 3 | 99.5 |
| *Aspergillus ustus* | | | | |
| UAMH 9479 | | | | |
| IMI 192b | 0 | 1 | 1 | 99.8 |

Number of nucleotide differences in ITS 1, 5.8S and ITS 2 within a single species. Column group "No. of nucleotide base differences" spans ITS1, ITS 2 and ITS1-5.8S- ITS 2.

Abbreviations: ATCC, American Type Culture Collection; IMI, Invasive Moulds Infections (UNMC); UAMH, University of Alberta Microfungus Collection and Herbarium.
[a]Deposited into GenBank Emericella nidulans.
[b]Deposited into the American Type Culture Collection as ATCC 201953.

Sequence Similarity of Clinical Isolates and Reference Strains of the Same Species The results of comparisons between clinical isolates and referenced strain sequences of the same Aspergillus species are shown in Table 3. The greatest intra-species variation was seen among isolates of *A. fumigatus* and isolates of *A. niger*. For both species, 5 nucleotide base differences existed between the sequence of clinical isolates and the referenced strain. Considering the length of the ITS region amplified, the overall sequence similarity was greater than 99% between the referenced Aspergillus strains and clinical isolates of the same species.

Sequence Comparisons with Other True Pathogenic and Opportunistic Fungi

To evaluate the utility of ITS sequences for identification of true pathogenic and opportunistic fungi, the ITS 1, 5.8S, and ITS 2 region sequences of 12 different genera known to cause infection in humans were determined in our laboratory and compared to sequences from the six medically important aspergilli. The results obtained with *A. fumigatus* are shown in Table 4. In comparison with *A. fumigatus*, sequence similarities among listed genera ranged from 50.2% to 89.6%, with Penicillium species showing the greatest sequence similarity. BLAST search comparisons were also made between the other medically important Aspergillus species and all opportunistic fungi available in the GenBank database (data not shown). The ITS 1 and 2 sequences of the referenced Aspergillus species differed from the other fungal genera by at least 1%, with one exception; *A. niger* ITS sequences had 99% sequence similarity with Arthrobotrys species and *Gliocladium cibotii*. As expected, the referenced *A. niger* sequence was listed first in the bit score rank listing. To further test the system, the sequences of clinical isolates of *A. niger* were compared using an ungapped BLAST search of the GenBank database. In each case, the clinical isolate was distinguished from Arthrobotrys species, and *Gliocladium cibotii* on the basis of bit score.

TABLE 4

Nucleotide base difference of ITS 1-5.8S-ITS 2 between *A. fumigatus* and other medically important fungal genera.

| Species and accession number | No. of nucleotide base differences ITS 1 | ITS 2 | ITS 1-5.8S-ITS 2 | # similarity[a] |
|---|---|---|---|---|
| *Ajellomyces capsulatus* | | | | |
| AF038353 | 93 | 45 | 143 | 76.6 |
| AF156892b | 86 | 59 | 150 | 76.7 |
| *Ajellomyces dermatitidis* | | | | |
| AF038355 | 93 | 66 | 163 | 74.1 |
| *Candida albicans* | | | | |
| AF217609b | 108 | 98 | 221 | 65.0 |
| L28817 | 97 | 98 | 211 | 64.8 |
| *Cladophialaphora bantiana* | | | | |
| AF131079b | 82 | 111 | 202 | 68.1 |
| *Cryptococcus neaformans* | | | | |
| AF162916b | 99 | 123 | 237 | 59.1 |
| L14067 | 53 | 126 | 193 | 59.4 |
| *Cylindrocarpon lichenicola* | | | | |
| AF133845b | 102 | 79 | 185 | 69.2 |
| *Fusarium oxysporum* | | | | |
| AF132799 | 85 | 91 | 180 | 62.3 |
| *Fusarium solanii* | | | | |
| U38558 | 100 | 92 | 202 | 66.7 |
| *Fusarium spp.* | | | | |
| IMI 183 | 99 | 89 | 197 | 67.0 |
| *Gymnascella hyalinospora* | | | | |
| AF129854b | 87 | 57 | 149 | 76.3 |
| *Penicillium capsulatum* | | | | |
| AF033429 | 44 | 23 | 70 | 88.0 |
| *Penicillium glabrum* | | | | |
| AF033407 | 39 | 22 | 62 | 89.6 |
| *Penicillium marnefeii* | | | | |
| ATCC 18224c | 60 | 57 | 124 | 79.1 |
| L37406 | 57 | 54 | 116 | 79.5 |
| *Phialophora verrucosa* | | | | |
| AF050281 | 78 | 104 | 196 | 67.5 |
| *Pseudallescheria boydii* | | | | |
| AF022486 | 106 | 131 | 248 | 55.6 |
| AF181558b | 109 | 132 | 252 | 55.4 |
| *Saccharomyces cerevisiae* | | | | |
| Z95929 | 144 | 146 | 302 | 50.2 |

Clinical Validation of ITS Sequence Analysis

To determine the utility of the ITS sequence for accurate identification of Aspergillus species, a blinded comparison was made using 11 morphologically confirmed Aspergillus clinical isolates. Following incubation of the culture plate for 24 hours at 30° C., and direct sequencing of PCR amplicons, ITS sequences were used in an ungapped BLAST search of the GenBank database. Identification of the unknown sequences was made using the highest bit score of listed species. Using this method, each of the coded specimens was identified correctly as the appropriate Aspergillus species. All of the identifications were made in less than 48 hours after receipt of the blinded culture plate.

Discussion

The increasing frequency of invasive fungal infection and the high mortality associated with disseminated fungal disease has highlighted the need for rapid identification of infectious,molds from clinical samples. The number of cases of invasive aspergillosis (IA) found at autopsy has increased 14-fold since 1978 (8). Early recognition and treatment of patients with invasive fungal infection is crucial, as the progression of invasive disease from detection to death is typically less than 14 days (4, 25). The present work was based on the premise that identification of Aspergillus at the species level will have clinical importance in the future. Currently, physicians rely on clinical findings and administer amphotericin B (AmB) empirically to immunosuppressed patients with sign and symptoms consistent with a fungal infection. However, the resistance of certain Aspergillus species to antifungal agents complicates empiric treatment for invasive disease (4, 14, 16). The effectiveness of AmB varies significantly depending on the species of Aspergillus, with over 95% of *A. terreus* isolates reported as resistant (10, 17, 22). Susceptibility testing has revealed a wide range of AmB MIC values; from 0.5 μg/ml for *A. niger* and *A. fumigatus* to 16 μg/ml for *A. flavus* and *A. nidulans*. Thus, rapid diagnosis and recognition of the species causing infection and treatment with the most active antifungal therapy may be important to reducing the mortality of immunosuppressed patients with IA.

The detection of Aspergillus DNA has been accomplished from blood, serum, bronchoalveolar lavage fluid, and tissue using the 18S rRNA gene as the target (6, 12, 24, 28). Einsele et al. detected Aspergillus DNA from blood approximately four days prior to the appearance of pulmonary infiltrates consistent with fungi by CT scan in patients with presumed aspergillosis (6). While their report detailed the shortened time-span to positive identification of Aspergillus from patient material, it was not possible to identify Aspergillus at the species level using the 18S rRNA gene (12). Additionally, the identification of aspergilli by PCR in some patient specimens, such as bronchoalveolar lavage fluid, does not always indicate invasive disease and therefore the use of PCR for detection of fungi in specimens from potentially colonized sites may be limited.

The ITS regions have been used as targets for phylogenetic analysis because they generally display sequence variation between species, but only minor variation within strains of the same species (11, 13, 20, 21). Shin et al. have described a fluorescent DNA probe assay using the ITS 2 region for the identification of Candida species (19). Their approach was reliable for the detection of Candida, as 95.1% of Candida isolates tested were identified to the species level with 100% specificity. In addition, species-level identification of six medically relevant Trichosporon isolates was achieved using a highly variable 12 bp region within the ITS 1 and 2 regions (21). Gaskell et al investigated sequence variation in ITS regions to distinguish Aspergillus from other allergenic molds (7). They found little variation between Aspergillus and Penicillium within the ITS 2 region but concluded the ITS 1 region may be sufficient for identification. Although *Penicillium capsulatum* and *P. glabrum* exhibited the highest sequence similarity to Aspergillus species in our study, the presence of a 10 bp sequence variation within the ITS 2 region allowed these species to be readily distinguished. We therefore concluded that both the ITS 1 and 2 regions were necessary for species-level identification. A limited number of strains were available for some Aspergillus species, particularly *A. ustus*, which was not previously listed in the GenBank database. Although incomplete, the sequence of GenBank sequences of non-referenced strains showed little difference from ATCC referenced strains.

Variation in ITS 2 amplicon size was used by Turenne et al. to identify clinically important fungi using capillary electrophoresis (CE) for separation and identification (23). They tested 56 fungi and were able to identify 48 at the species level. Similar to our results, they found only a two nucleotide base difference when comparing the length of *A. flavus, A. niger*, and *Fusarium solani* ITS amplicons. This suggested that amplicon length may not be sufficiently different to distinguish species. We also found *A. niger* and *A. terreus* amplicons to be similar in length. The resolution of CE is approximately two nucleotides for amplicons greater than 250 bases in length. It is not clear whether the technical limitations of CE make it a reliable method for species-level identification of Aspergillus.

The comparison of ITS 1-5.8S-ITS 2 region sequences between referenced and clinical isolates of six Aspergillus species revealed several areas of sequence variation. The inclusion of the 5.8S rRNA gene sequence had minimal impact on the overall comparison since there is little interspecies variation in this region. In our study, the intraspecies variation among clinical and pathogenic referenced Aspergillus strains was less than 1%. This is consistent with the phylogenetic study by Sugita, et al. of the Trichosporon species where less than 1% of nucleotide bases were different among various strains of the same species (21).

Gaskell et al. have previously shown that Alternaria, Penicillium, Cladosporium, and Aspergillus could be differentiated at the genus level on the basis of ITS sequence analysis (7). The question remained however, whether ITS sequences could be used to identify any fungus that may be recovered clinically, including those that may be environmental contaminants. In our study, a BLAST search of all GenBank sequences was conducted using the six referenced Aspergillus species ITS sequences. Sequence similarities of less than 89.6% were seen when comparing the ITS region sequences of *A. fumigatus* to those of other genera, including opportunistic fungi or true pathogenic fungi listed in Table 4. This search also identified 2 species, *A. nidulans* and *A. niger*, that had sequence similarity of 99% with other opportunistic fungi.

*A. nidulans* (deposited in GenBank as *Emericella nidulans*) ITS sequences had 99% sequence similarity with *Emericella quadrilineata*. However, *E. quadrilineata* has not been reported as a cause of invasive disease in humans. *A. niger* ITS sequences were found to be similar to non-referenced isolates of *A. phoenicis, A. tubigensis*, Arthrobotrys species, and *Gliocladium cibotii*. The *A. niger* aggregate includes two subgroups and at least 14 species, including *A. phoenicis* and *A. tubigensis*, that are morphologically indistinguishable. By contrast, Gliocladium and Arthrobotrys species have morphological features distinct from *A. niger*. Again, none of these species have been associated with invasive disease and their medical importance is unknown (18). Additional studies are in progress to confirm the ITS sequences of referenced isolates of these infrequently encountered fungal species. Overall, the present results showed that ITS sequence analysis can be used to exclude fungal genera which may be considered in the differential diagnosis of a patient with invasive mycosis. However, the sequence similarity of 99% with some genera and species indicated that the BLAST bit score would be needed to identify clinical isolates of Aspergillus to the species level. A correct identification of clinical isolates of *A. niger* and *A. nidulans* was made using the highest bit score of listed species from the BLAST search. This demonstrated that ITS 1 and 2 sequence analysis can be used for recognition of many fungal genera, including those that do not typically cause invasive disease such as airborne allergenic fungi.

Our studies showed that it was not necessary to clone the PCR products to obtain an accurate reading of the sequence. The elimination of this step allowed for direct automated sequencing of PCR products and significantly reduced the amount of time involved in obtaining a result. The ability to sample small (approximately 2 $mm^2$) portions of the culture contributed significantly to rapid identification. Colonies of this size generally cannot be used for morphologic identification and in most cases the specimen must be incubated for 5 days or longer. The ability to rapidly and accurately identify Aspergillus species from blinded samples, with results available within 48 h, confirmedthe value of this approach. Several issues may affect the time required to obtain a result, including the availability of a dedicated sequencer. The need to repeat the sequencing procedure due to gel compression or contamination may also delay the process. Although automated sequencing and analysis provided accurate discrimination of Aspergillus from other fungi, a probe based DNA hybridization approach has been described for other organisms and may be more cost effective in the future (6, 19).

Identification of medically important Aspergillus species from short-term culture using nucleic acid sequence analysis of the ITS 1 and 2 regions in combination with a BLAST bit score, is a reliable and efficient method that provides earlier identification than standard culture methods. The identification of rarely encountered opportunistic organisms following sequence analysis should prompt a review of the sequence data and correlation with clinical findings. Investigations are in progress to determine whether the method has utility for direct identification of fungi in tissue sections where histologic evidence of a fungus exists. Additional studies are needed to demonstrate whether identification of Aspergillus at the species level will improve patient outcome through the selection of more effective antifungal therapy.

EXAMPLE 2

Internal Transcribed Spacer Region Sequences for Identifying Additional Clinically Relevant Species of Fungus As demonstrated in Example 1 use of a universal primer set to amplify the ITS regions of the fungal rRNA gene followed by sequence analysis of the resulting amplicon facilitates thespecies specific identification of fungi. Additional sequences have been determined using the described primers for the additional fungi listed in Addendum 1.

ADDENDUM 1

SEQ ID NO: 1
5' primer ITS 1th
GGAAGTAAAAGTCGTAACAAGG
SEQ ID NO: 2
3' primer ITS 4th
GTATCCCTACCTGATCCGAGG
SEQ ID NO: 3
*Aspergillus ustus* GenBank Accession No: AF157507
GGAAGTAAAAGTCGTAACAAGGTTTCTGTAGGTGAACCTGCAGAAGGATCATTAGTGAAAGCA
AGGGCCAGCCATACGGACGGCGCTACTCGCGTACAACGTCTCTGGCGTCCGTAGGTGAACCTG
CGGAAGGATCATTACCGAGTGCAGGTCTGCCCCGGGCAGGCCTAACCTCCCACCCGTGAATAC
CTGACCAACGTTGCTTCGGCGGTGCGCCCCTCCGGGGGTAGCCGCCGGAGACCACACCGAACC
TCCTGTCTTTAGTGTTGTCTGAGCTTGATAGCAAACCTATTAAAACTTTCAACAATGGATCTC
TTGGTTCCGGCATCGATGAAGAACGCAGCGAACTGCGATAAGTAATGTGAATTGCAGAATTCA
GTGAATCATCGAGTCTTTGAACGCACATTGCGCCCCCTGGCATTCCGGGGGGCATGCCTGTCC
GAGCGTCATTGCTGCCCTTCAAGCCCGGCTTGTGTGTTGGGTCGTCGTCCCCTCCGGGGGACG
GGCCCGAAAGGCAGCGGCGGCACCGCGTCCGGTCCTCGAGCGTATGGGGCTTTGTCACCCGCT
CGATTAGGGCCGGCCGGGCGCCAGCCGGCGTCTCCAACCTTTTATTTTACCAGGTTGACCTCG
GATCAGGTAGGGATAC
SEQ ID NO: 4
*Aspergillus terreus* Genbank Accession No: AF138290
GGAAGTAAAAGTCGTAACAAGGTTTCTGTAGGTGAACCTGCAGAAGGATCATTAGTGAAAGCA
AGGGCCAGCCATACGGACGGCGCTACTCGCGTACAACGTCTCTGGCGTCCGTAGGTGAACCTG
CGGAAGGATCATTACCGAGTGCGGGTCTTTATGGCCCAACCTCCCACCCGTGACTATTGTACC
TTGTTGCTTCGGCGGGCCCGCCAGCGTTGCTGGCCGCCGGGGGGCGACTCGCCCCCGGGCCCG
TGCCCGCCGGAGACCCCAACATGAACCCTGTTCTGAAAGCTTGCAGTCTGAGTGTGATTCTTT
GCAATCAGTTAAAACTTTCAACAATGGATCTCTTGGTTCCGGCATCGATGAAGAACGCAGCGA
AATGCGATAACTAATGTGAATTGCAGAATTCAGTGAATCATCGAGTCTTTGAACGCACATTGC
GCCCCCTGGTATTCCGGGGGGCATGCCTGTCCGAGCGTCATTGCTGCCCTCAAGCCCGGCTTG
TGTGTTGGGCCCTCGTCCCCCGGCTCCCGGGGGACGGGCCCGAAAGGCAGCGGCGGCACCGCG
TCCGGTCCTCGAGCGTATGGGGCTTCGTCTTCCGCTCCGTAGGCCCGGCCGGCGCCCGCCGAC
GCATTTATTTGCAACTTGTTTTTTTCCAGGTTGACCTCGGATCAGGTAGGGATAC
SEQ ID NO: 5
*Aspergillus niger* GenBank Accession No: AF138904
GGAAGTAAAAGTCGTAACAAGGTTTCTGTAGGTGAACCTGCAGAAGGATCATTAGTGAAAGCA
AGGGCCAGCCATACGGACGGCGCTACTCGCGTACAACGTCTCTGGCGTCCGTAGGTGAACCTG
CGGAAGGATCATTACCGAGTGCGGGTCCTTTGGGCCCAACCTCCCATCCGTGTCTATTGTACC
CTGTTGCTTCGGCGGGCCCGCCGCTTGTCGGCCGCCGGGGGGGCGCCTCTGCCCCCCGGGCCC
GTGCCCGCCGGAGACCCCAACACGAACACTGTCTGAAAGCGTGCAGTCTGAGTTGATTGAATG
CAATCAGTTAAAACTTTCAACAATGGATCTCTTGGTTCCGGCATCGATGAAGAACGCAGCGAA
ATGCGATAACTAATGTGAATTGCAGAATTCAGTGAATCATCGAGTCTTTGAACGCACATTGCG
CCCCCTGGTATTCCGGGGGGCATGCCTGTCCGAGCGTCATTGCTGCCCTCAAGCCCGGCTTGT
GTGTTGGGTCGCCGTCCCCCTCTCCGGGGGGACGGGCCCGAAAGGCAGCGGCGGCACCGCGTC
CGATCCTCGAGCGTATGGGGCTTTGTCACATGCTCTGTAGGATTGGCCGGCGCCTGCCGACGT
TTTCCAACCATTCTTTCCAGGTTGACCTCGGATCAGGTAGGGATAC
SEQ ID NO: 6
*Aspergillus nidulans* GenBank Accession No: AF138288
GGAAGTAAAAGTCGTAACAAGGTTTCTGTAGGTGAACCTGCAGAAGGATCATTAGTGAAAGCA
AGGGCCAGCCATACGGACGGCGCTACTCGCGTACAACGTCTCTGGCGTCCGTAGGTGAACCTG
CGGAAGGATCATTACCGAGTGCGGGCTGCCTCCGGGCGCCCAACCTCCCACCCGTGACTACTA
ACACTGTTGCTTCGGCGGGGAGCCCCCCAGGGGCGAGCCGCCGGGGACCACTGAACTTCATGC
CTGAGAGTGATGCAGTCTGAGCCTGAATACAAATCAGTCAAAACTTTCAACAATGGATCTCTT
GGTTCCGGCATCGATGAAGAACGCAGCGAACTGCGATAAGTAATGTGAATTGCAGAATTCAGT
GAATCATCGAGTCTTTGAACGCACATTGCGCCCCCTGGCATTCCGGGGGGCATGCCTGTCCGA
GCGTCATTGCTGCCCTCAAGCCCGGCTTGTGTGTTGGGTCGTCGTCCCCCCCGGGGGACGGGC
CCGAAAGGCAGCGGCGGCACCGTGTCCGGTCCTCGAGCGTATGGGGCTTTGTCACCCGCTCGA
TTAGGGCCGGCCGGGCGCCAGCCGGCGTCTCCAACCTTATTTTTCTCAGGTTGACCTCGGATC
AGGTAGGGATAC
SEQ ID NO: 7
*Aspergillus fumigatus* GenBank Accession No: AF138288
GGAAGTAAAAGTCGTAACAAGGTTTCTGTAGGTGAACCTGCAGAAGGATCATTAGTGAAAGCA
AGGGCCAGCCATACGGACGGCGCTACTCGCGTACAACGTCTCTGGCGTCCGTAGGTGAACCTG
CGGAAGGATCATTACCGAGTGAGGGCCCTTTGGGTCCAACCTCCCACCCGTGTCTATCGTACC
TTGTTGCTTCGGCGGGCCCGCCGTTTCGACGGCCGCCGGGGAGGCCTTGCGCCCCCGGGCCCG
CGCCCGCCGAAGACCCCAACATGAACGCTGTTCTGAAAGTATGCAGTCTGAGTTGATTATCGT
AATCAGTTAAAACTTTCAACAACGGATCTCTTGGTTCCGGCATCGATGAAGAACGCAGCGAAA
TGCGATAACTAATGTGAATTGCAGAATTCAGTGAATCATCGAGTCTTTGAACGCACATTGCGC
CCCCTGGTATTCCGGGGGGCATGCCTGTCCGAGCGTCATTGCTGCCCTCAAGCACGGCTTGTG
TGTTGGGCCCCCGTCCCCCTCTCCCGGGGGACGGGCCCGAAAGGCAGCGGCGGCACCGCGTCC
GGTCCTCGAGCGTATGGGGCTTTGTCACCTGCTCTGTAGGCCCGGCCGGCGCCAGCCGACACC
CAACTTTATTTTTCTAAGGTTGACCTCGGATCAGGTAGGGATAC
SEQ ID NO: 8
*Aspergillus flavus* GenBank Accession No: AF138287
GGAAGTAAAAGTCGTAACAAGGTTTCTGTAGGTGAACCTGCAGAAGGATCATTAGTGAAAGCA
AGGGCCAGCCATACGGACGGCGCTACTCGCGTACAACGTCTCTGGCGTCCGTAGGTGAACCTG
CGGAAGGATCATTACCGAGTGTAGGGTTCCTAGCGAGCCCAACCTCCCACCCGTGTTTACTGT
ACCTTAGTTGCTTCGGCGGGCCCGCCATTCATGGCCGCCGGGGGCTCTCAGCCCCGGGCCCGC
GCCCGCCGGAGACACCACGAACTCTGTCTGATCTAGTGAAGTCTGAGTTGATTGTATCGCAAT
CAGTTAAAACTTTCAACAATGGATCTCTTGGTTCCGGCATCGATGAAGAACGCAGCGAAATGC ADDENDUM 1-continued GATAACTAGTGTGAATTGCAGAATTCCGTGAATCATCGAGTCTTTGAACGCACATTGCGCCCC
CTGGTATTCCGGGGGGCATGCCTGTCCGAGCGTCATTGCTGCCCATCAAGCACGGCTTGTGTG
TTGGGTCGTCGTCCCCTCTCCGGGGGGGACGGGCCCCAAAGGCAGCGGCGGCACCGCGTCCGA
TCCTCGAGCGTATGGGGCTTTGTCACCCGCTCTGTAGGCCCGGCCGGCGCTTGCCGAACGCAA
ATCAATCTTTTTCCAGGTTGACCTCGGATCAGGTAGGGATAC

SEQ ID NO: 9

*Pseudallescheria boydii* GenBank Accession No: AF181558

GGAAGTAAAAGTCGTAACAAGGTTTCTGTAGGTGAACCTGCAGAAGGATCATTAGTGAAAGCA
AGGGCCAGCCATACGGACGGCGCTACTCGCGTACAACGTCTCTGGCGTCCGTAGGTGAACCTG
CGGAGGGATCATTACAGAGTTACTACTCCAAACCCATTGTGGGAAGTAAAAGTCGTAACAAGG
TTTCTGTAGGTGAACCTGCAGAAGGATCATTAGTGAAAGCAAGGGCCAGCCATACGGACGGCG
CTACTCGCGTACAACGTCTCTGGCGAACCTTACCTATGTTCTGTTGCCTCGGCGGCGTGGTCA
GCGCCCCCTCTGAAAAGAGGACGATGTCCTCCCGCCGGCAGCACCAAACTCTTTGAATTTTAC
AGCGGATCACAGTTCTGATTTGAAAACAAAAAACAAGTTAAAACTTTCAACAACGGATCTCTT
GGTTCTGGCATCGATGAAGAACGCAGCGAAATGCGATAAGTAATGTGAATTGCAGAATTCAGT
GAATCATCGAATCTTTGAACGCACATTGCGCCCGGCAGTAATCTGCCGGGCATGCCTGTCCGA
GCGTCATTTCAACCCTCGAACCTCCGTTTCCTCAGGGAAGCTCAGGGTCGGTGTTGGGGCGCT
ACGGCGAGTCTTCGCGACCCTCCGTAGGCCCTGAAATACAGTGGCGGTCCCGCCGCGGTTGCC
TTCTGCGTAGTAAGTCTCTTTTGCAAGCTCGCATTGGGTCCCGGCGGAGGCCTGCCGTCAAAC
CACCTATAACTCCAGATGGTTGACCTCGGATCAGGTAGGGTAC

SEQ ID NO: 10

*Fusarium solani* GenBank Accession No: AF165874
(deposited as *Nectria haemotococca*)

GGAAGTAAAAGTCGTAACAAGGTTTCTGTAGGTGAACCTGCAGAAGGATCATTCGAGTTATAC
AACTCATCAACCCTGTGAACATACCTATAACGTTGCCTCGGCGGGAACAGACGGCCCCGTAAC
ACGGGCCGCCCCCGCCAGAGGACCCCCTAACTCTGTTTCTATAATGTTTCTTCTGAGTAAACA
AGCAAATAAATTAAAACTTTCAACAACGGATCTCTTGGCTCTGGCATCGATGAAGAACGCAGC
GAAATGCGATAAGTAATGTGAATTGCAGAATTCAGTGAATCATCGAATCTTTGAACGCACATT
GCGCCCGCCAGTATTCTGGCGGGCATGCCTGTTCGAGCGTCATTACAACCCTCAGGGCCCCGG
GCCTGGCGTTGGGGATCGGCGGAAGCCCCCTGCGGGCACAACGCCGTCCCCCAAATACAGTGG
CGGGGCCCGCCGCAAACTTCCATTGCGGTANATATACTAACACCTCGCAAATGGAGAGAGGGG
GCGGCCACGCCGTAAAACACCCAACTTCTGAATGTTGACCTCGAATCAAGTAGGAATAC

SEQ ID NO: 11

*Fusarium oxysporum* GenBank Accession No: AF165875

GGAAGTAAAAGTCGTAACAAGGTTTCTGTAGGTGAACCTGCAGAAGGATCATTAGTGAAAGCA
AGGGCCAGCCATACGGACGGCGCTACTCGCGTACAACGTCTCTGGCGTCCGTAGGTGAACCTG
CGGTGGGTCATTACCGAGTTTACAACTCCCAAACCCCTGTGAACATACCACTTGTTGCCTCGG
CGGATCAGCCCGCTCCCGGTAAAACGGGACGGCCCGCCAGAGGACCCCTAAACTCTGTTTCTA
TATGTAACTTCTGAGTAAAACCATAAATAAATCAAAACTTTCAACAACGGATCTCTTGGTTCT
GGCATCGATGAAGAACGCAGCAAAATGCGATAAGTAATGTGAATTGCAGAATTCAGTGAATCA
TCGAATCTTTGAACGCACATTGCGCCTGCCAGTATTCTGGCGGGCATGCCTGTTCGAGCGTCA
TTTCAACCCTCAAGCACAGCTTGGTGTTGGGACTCGCGTTAATTCGCGTTCCCCAAATTGATT
GGCGGTCACGTCGAGCTTCCATAGCGTAGTAGTAAAACCCTCGTTACTGGTAATCGTCGCGGC
CACGCCGTTAAACCCCAACTTCTGAATGTTGACCTCGGATCAGGTAGGAATAC

SEQ ID NO: 12

*Fusarium monilliformes* GenBank Accession No: AF165873

GGAAGTAAAAGTCGTAACAAGGTTTCTGTAGGTGAACCTGCAGAAGGATCATTAGTGAAAGCA
AGGGCCAGCCATACGGACGGCGCTACTCGCGTACAACGTCTCTGGCGTCCGTAGGTGAACCTG
CGGAGGGATCATTACAGAGTTACTACAACTCCCAAACCCCTGTGAACATACGAATTGTTGCCT
CGGCGGATCAGCCCGCTCCCGGTAAAACGGGACGGCCCGCCAGAGGACCCCTAAACTCTGTTT
CTATATGTAACTTCTGAGTAAAACCATAAATAAATCAAAACTTTCAACAACGGATCTCTTGGT
TCTGGCATCGATGAAGAACGCAGCAAAATGCGATAAGTAATGTGAATTGCAGAATTCAGTGAA
TCATCGAATCTTTGAACGCACATTGCGCCCGCCAGTATTCTGGCGGGCATGCCTGTTCGAGCG
TCATTTCAACCCTCAAGCCCCCGGGTTTGGTGTTGGGGATCGGCGAGCCCTTGCGGCAAGCCG
GCCCCGAAATCTAGTGGCGGTCTCGCTGCAGCTTCCATTGCGTAGTAGTAAAACCCTCGCAAC
TGGTACGCGGCGCGGCCAAGCCGTTAAACCCCCAACTTCTGAATGTTGACCTCGGATCAGGTA
GGAATAC

SEQ ID NO: 13

*Malassezia furfur* GenBank Accession No: AF246896

GGAAGTAAAAGTCGTAACAAGGTTTCTGTAGGTGAACCTGCAGAAGGATCATTAGTGAAAGCA
AGGGCCAGCCATACGGACGGCGCTACTCGCGTACAACGTCTCTGGCGCCCAACTTTACACAAT
ATCCACAAACCCGTGTGCACCGTTTGGATGAGTTGGACCTCGCAAGAGGCTCGGCTCTCCAAT
CCATTTCTACCAAACTCGTATGGTTTGTATGAACGTGGAAATCGTTGGACCGTAACTGGCCAA
CAACCAATAATACAACTTTCGACAACGGATCTCTTGGTTCTCCCATCGATGAAGAACGCAGCG
AAACGCGATAGGTAATGTGAATTGCAGAATTCCGTGAATCATCGAATCTTTGAACGCACCTTG
CGCTCCATGGTATTCCGTGGAGCATGCCTGTTTGAGTGCCGTGAATTCTCTCTCCCCAAGCGG
TTGCGATTGCACTGCTTTGGCGGACGAGGTTGGATGGGTGCTTCTGCCTGTTTCGCAAGAAAC
AGGCTCGCCCGAAATGCATTAGCGCCTTTGGGACACACTCTGCAAACCGCTCTTGAAAGGGGA
AGGCCGGCAGAAGGGGATGGAGGAACTCCGCCCGTCAGCTATACCTCGGATCAGGTAGGGATA
C

SEQ ID NO: 14

*Cylindrocarpon lichenicola* GenBank Accession No: AF133843

GGAAGTAAAAGTCGTAACAAGGTTTCTGTAGGTGAACCTGCAGAAGGATCATTAGTGAAAGCA
AGGGCCAGCCATACGGACGGCGCTACTCGCGTACAACGTCTCTGGCGTCCGTAGGTGAACCTG
CGGAAGGATCATTACACAAATATGAAGGCGGGCTGGAACCTCTCGGGGTTACAGCCTTGCTGA
ATTATTCACCCTTGTCTTTTGCGTACTTCTTGTTTCCTTGGTGGGTTCGCCCACCACTAGGAC
AAACATAAACCTTTTGTAATTGCAATCAGCGTCAGTAACAAATTAATAATTACAACTTTCAAC
AACGGATCTCTTGGTTCCGGCATCGATGAAGAACGCAGCGAAATGCGATAAGTAATGTGAATT
GCAGAATTCCGTGAATCATCGAATCTTTGAACGCACATTGCGCCCTTTGGTATTCCGGGGGGC

ADDENDUM 1-continued

ATGCCTGTCCGAGCGTCATTTGTACCCTCAAGCTTTGCTTGGTGTTGGGCGTCTTGTCTCTAG
CTTTGCTGGAGACTCGCCTTAAAGTAATTGGCAGCCGGCCTACTGGTTTCGGAGCGCAGCACA
AGTCGCACTCTCTATCAGCAAAGGTCTAGCATCCATTAAGCCTTTTTTCAACTTTTGACCTC
GGATCAGGTAGGGATACC

SEQ ID NO: 15
*Cladophialophora bantiana* GenBank Accession No: AF131079
GGAAGTAAAAGTCGTAACAAGGTTTCCGTAGGTGAACCTGCGGAAGGATCATTAACGAGTTAG
GGTCTCCCAGGCCCGGCCGGAAGTAAAAGTCGTAACAAGGTTTCTGTAGGTGAACCTGCAGAA
GGATCATTAGTGAAAGCAAGGGCCAGCCATACGGACGGCGCTACTCGCGTACAACGTCTCTGG
CGTCCCAACCCTTTGTTTATTAAACCTCTGTTGCTTCGGCGGACCCGTCTTCCCTGACCGCCG
GAGGACCGCCGACTCGGCGTCCTCTGGCCAGCGTCCGCCGGGGGCCTCTTCTCCAAACTCTGG
TTAAGCATGATTTTGTGTCTGAGTGATTTGTATCAAATCAAAAGCAAAAACTTTCAACAACGG
ATCTCTTGGTTCTGGCATCGATGAAGAACGCAGCGAAATGCGATAAGTAATGCGAATTGCAGA
ATTCCAGTGAGTCATCGAATCTTTGAACGCACATTGCGCCCTTTGGTATTCCGAAGGGCATGC
CTGTTCGAGCGTCATTATCACCCCTCAAGCCCTCGTGCTTGGTGTTGGACGGTCTGGCGGAAG
TGTCGTGCACCCCGCCCCTCCTAAAGACAATGACGGCGGCCTCGTGGAACCCCCGGTACACTG
AGCTTCTTTACCGAGCACGTATCGGATCAAGGGCGCCCGGGACACGGTCTTCTCCCTCATGTG
GGAAACATTGCAAGGTTGACCTCGGATCAGGTAGGAATACG SEQ ID NO: 16
*Gymnascella hyalinaspora* GenBank Accession No: AF129854
GGAAGTAAAAGTCGTAACAAGGTTTCTGTAGGTGAACCTGCAGAAGGATCATTAGTGAAAGCA
AGGGCCAGCCATACGGACGGCGCTACTCGCGTACAACGTCTCTGGCGTCCGTAGGTGAACCTG
CGGAAGGATCATTACAGTGCCGCCGGGACGCGCCCCCTAAACCGGGGCGTGCTCCCGCAACTG
GCCACCCGTGTCTACCGAACCTCGTTGCTTTGGCGGGCCCGCGAACCCCTCACGGGGGGAGCC
GCCTTGGGGAGCAGTCCCCGGGCCCGCGCCCGCCAGAGAACCACAACTGAACTCTTTGCTGAT
GAGTGACTGTCTGAGTGATTGATTTAATCATTAAAACTTTCAACAACGGATCTCTTGGTTCCA
GCATCGATGAAGAACGCAGCGAAATGCGATAAGTAATGTGAATTGCAGAATTCCGTGAATCAT
CGAATCTTTGAACGCACATTGCGCCCTCTGGTATTCCGGGGGGCATGCCTGTCCGAGCGTCAT
TGCACCAATCAAGCCCGGCTTGTGTGATGGGTCTTCATTCGTCCCGAATGGGGGACGGCCCG
AAATGCAGTGGCGGCGTCGTGGTTATCCAACGGCCTGAGTGTATGGGGCTCTGTCACACGCTC
ACCAGCCAGGACCGGCGCCAGCCTACCAGTCTATTCTTCTTAGGTTGACCTCGGATCAGGTAG
GGATACC SEQ ID NO: 17
*Blastomyces dermatitides* GenBank Accession No: AF183912
(deposited as *Ajellomyces dermatitidis*)
GGAAGTAAAAGTCGTAACAAGGTTTCTGTAGGTGAACCTGCAGAAGGATCATTAGTGAAAGCA
AGGGCCAGCCATACGGACGGCGCTACTCGCGTACAACGTCTCTGGCGTTAACGCGCCGNGGGG
GGTTGGACCTCCTAGACCGGAGGAACCCCGGCCCCCTCACCTGGCCACCCTTGTCTATTTTA
CCTGTTGCTTCGGCGGGCCTGCAGCGATGCTGCCGGGGGAGTTTTCACTCCCCGGGCTCGTGC
CCGCCGAGGACACCGCTAGAACTTCTGGTGAACGATTGACATCTGAGAAAATAACTATAATCA
GTTAAAACTTTCAACAACGGATCTCTTGGTTCCGACATCGATGAAGAACGCAGCGAAATGCGA
TAAGTAATGTGAATTGCAGAATTCCGTGAATCATCGAATCTTTGAACGCACATTGCGCCCTCT
GGTATTCCGGGGGGCATGCCTGTCCGAGCGTCATTGCAACCCTCAAGCGCGGCTTGTGTGTTG
GGCCTTCGTCCCCCCGTGGACGTGCCCGAAATGCAGCGGCGGCGTCGTGTTCCGGTGCCCGAG
CGTATGGGGCTTTGTCACCCGCTCTAGAGGCCCGGCCGGCTCCGGCCCCATCTCAAACCCTTC
GAGGGAGGGCGGTCTTCGGGCCGGTCTCCCCACCAGGTTGACCTCGGATCAGGTAGGAATAC SEQ ID NO: 18
*Histoplasma duboisii* GenBank Accession No: AF162917
(deposited *Ajellomyces capsulatus*)
GGAAGTAAAAGTCGTAACAAGGTTTCTGTAGGTGAACCTGCAGAAGGATCATTAGTGAAAGCA
AGGGCCAGCCATACGGACGGCGCTACTCGCGTACAACGTCTCTGGCGTCCGTAGGTCGCCGTG
GGGGGTTGGGAGTCTCTGACCGGGACCCCTCCGCCCCCCTTACCCGGCCATCCTTGTCTACCG
GACCTGTTGCCTCGGCGGGCCTGCAGCGATGCTGCCGGGGGAGCTTCTTCTCCCCGGGCTCGT
GTCCGCCGGGGACACCGCAAGAACCGTCGGTGAACGATTGGCGTCTGAGCATAAGAGCGATAA
TAATCCAGTTAAAACTTTCAACAACGGATCTCTTGGTTCCGACATCGATGAAGAACGCAGCGA
AATGCGATAAGTAATGTGAATTGCAGAATTCCGTGAATCATCGAATCTTTGAACGCACATTGC
GCCCCCTGGTATTCCGGGGGGCATGCCTGTCCGAGCGTCATTGCAACCCTCAAGCGCGGCTTG
TGTTTTGGGCCGTCGTCCCCCCTCGACCGGCGGGACTTGCCCCGAAATGCAGTTGGCGGTGTC
GAGTTCCGGTTGCCCCGAGCGTTATGGCTTTGCCACCCGCTCTGGAAGCCC SEQ ID NO: 19
*Histoplasma capsulatum* GenBank Accession No: AF156892
(deposited as *Ajellomyces capsulatus*)
GGAAGTAAAAGTCGTAACAAGGTTTCTGTAGGTGAACCTGCAGAAGGATCATTAGTGAAAGCA
AGGGCCAGCCATACGGACGGCGCTACTCGCGTACAACGTCTCTGGCGTCCGTAGGTCGCCGTG
GGGGGTTGGGAGTCTCTGACCGGGACCCCTCCGCCCCCCTTACCCGGCCATCCTTGTCTACCG
GACCTGTTGCCTCGGCGGGCCTGCAGCGATGCTGCCGGGGGAGCTTCTTCTCCCCGGGCTCGT
GTCCGCCGGGGACACCGCAAGAACCGTCGGTGAACGATTGGCGTCTGAGCATAAGAGCGATAA
TAATCCAGTTAAAACTTTCAACAACGGATCTCTTGGTTCCGACATCGATGAAGAACGCAGCGA
AATGCGATAAGTAATGTGAATTGCAGAATTCCGTGAATCATCGAATCTTTGAACGCACATTGC
GCCCCCTGGTATTCCGGGGGGCATGCCTGTCCGAGCGTCATTGCAACCCTCAAGCGCGGCTTG
TGTTTTGGGCCGTCGTCCCCCCTCGACCGGCGGGACTTGCCCCGAAATGCAGTTGGCGGTGTC
GAGTTCCGGTTGCCCCGAGCGTTATGGCTTTGCCACCCGCTCTGGAAGCCC SEQ ID NO: 20
*Cryptococcus neoformans* GenBank Accession No: AF162916
GGAAGTAAAAGTCGTAACAAGGTTTCTGTAGGTGAACCTGCAGAAGGATCATTAGTGAAAGCA
AGGGCCAGCCATACGGACGGCGCTACTCGCGTACAACGTCTCTGGCGGAGAATATTGGACTTT
GGTCCATTTATCTACCCATCTACACCTGTGAACTGTTTATGTGCTTCGGCACGTTTTACACAA
ACTTCTAAATGTAATGAATGTAATCATATTATAACAATAATAAAACTTTCAACAACGGATCTC
TTGGCTTCCACATCGATGAAGAACGCAGCGAAATGCGATAAGTAATGTGAATTGCAGAATTCA ADDENDUM 1-continued GTGAATCATCGAGTCTTTGAACGCAACTTGCGCCCTTTGGTATTCCGAAGGGCATGCCTGTTT
GAGAGTCATGAAAATCTCAATCCCTCGGGTTTTATTACCTGTTGGACTTGGATTTGGGTGTTT
GCCGCGACCTGCAAAGGACGTCGGCTCGCCTTAAATGTGTTAGTGGGAAGGTGATTACCTGTC
AGCCCGGCGTAATAAGTTTCGCTGGGCCTATGGGGTAGTCTTCGGCTTGCTGATAACAACCAT
CTCTTTTTGT SEQ ID NO: 21
*Issatchenkia orientalis* GenBank Accession No: AF246989
GGAAGTAAAAGTCGTAACAAGGTTTCCGTAGGTGAACCTGCGGAAGGATCATTACTGTGATTT
AGTACTACACTGCGTGAGCGGAACGAAAACAACAACACCTAAAATGTGGAATATAGCATATAG
TCGACAAGAGAAATCTACGAAAAACAAACAAAACTTTCAACAACGGATCTCTTGGTTCTCGCA
TCGATGAAGAGCGCAGCGAAATGCGATACCTAGTGTGAATTGCAGCCATCGTGAATCATCGAG
TTCTTGAACGCACATTGCGCCCCTCGGCATTCCGGGGGGCATGCCTGTTTGAGCGTCGTTTCC
ATCTTGCGCGTGCGCAGAGTTGGGGGAGCGGAGCGGACGACGTGTAAAGAGCGTCGGAGCTGC
GACTCGCCTGAAAGGGAGCGAAGCTGGCCGAGCGAACTAGACTTTTTTTCAGGGACGCTTGGC
GGCCGAGAGCGAGTGTTGCGAGACAACAAAAAGCTCGACCTCAGATCAGGTAGGAAT SEQ ID NO: 22
*Candida albicans* GenBank Accession No: AF217609
GGAAGTAAAAGTCGTAACAAGGTTTCTGTAGGTGAACCTGCAGAAGGATCATTAGTGAAAGCA
AGGGCCAGCCATACGGACGGCGCTACTCGCGTACAACGTCTCTGGCGTCCGTAGGTGAACCTG
CGGAAGGATCATTACTGATTTGCTTAATTGCACCACATGTGTTTTTCTTTGAAACAAACTTGC
TTTGGCGGTGGGCCCAGCCTGCCGCCAGAGGTCTAAACTTACAACCAATTTTTTATCAACTTG
TCACACCAGATTATTACTAATAGTCAAAACTTTCAACAACGGATCTCTTGGTTCTCGCATCGA
TGAAGAACGCAGCGAAATGCGATACGTAATATGAATTGCAGATATTCGTGAATCATCGAATCT
TTGAACGCACATTGCGCCCTCTGGTATTCCGGAGGGCATGCCTGTTTGAGCGTCGTTTCTCCC
TCAAACCGCTGGGTTTGGTGTTGAGCAATACGACTTGGGTTTGCTTGAAAGACGGTAGTGGTA
AGGCGGGATCGCTTTGACAATGGCTTAGGTCTAACCAAAAACATTGCTTGCGGCGGTAACGTC
CACCACGTATATCTTCAAACTTTGACCTCAAATCAGGTAGGACTACCCGCTGAACTTAAGCAT
ATCAATAAGCGGAGGA SEQ ID NO: 23
*Candida lusitaniae* GenBank Accession No: AF172262
AAAAATACATTACACATTGTTTTTGCGAACAAAAAAATAAATTTTTTTATTCGAATTTCTTAA
TATCAAAACTTTCAACAACGGATCTCTTGGTTCTCGCATCGATGAAGAACGCAGCGAATTGCG
ATACGTAGTATGACTTGCAGACGTGAATCATCGAATCTTTGAACGCACATTGCGCCTCGAGGC
ATTCCTCGAGGCATGCCTGTTTGAGCGTCGCATCCCCTCTAACCCCCGGTTAGGCGTTGCTCC
GAAATATCAACCGCGCTGTCAAACACGTTTACAGCACGACATTTCGCCCTCAAATCAGGTAGG
ACTACCCG SEQ ID NO: 24
*Candida glabrata* GenBank Accession No: AF167993
AAGAATTTAATTGATTTGTCTGAGCTCGGAGAGAGACATCTCTGGGGAGGACCAGTGTGACAC
TCAGGAGGCTCCTAAAATATTTTCTCTTCTGTGAATGCTATTTCTCCTGCCTGCGCTTAAGTG
CGCGGTTGGTGGGTGTTCTGCAGTGGGGGGAGGGAGCCGACAAAGACCTGGGAGTGTGCGTGG
ATCTCTCTATTCCAAAGGAGGTGTTTTATCACACGACTCGACACTTTCTAATTACTACACACA
GTGGAGTTTACTTTACTACTATTCTTTTGTTCGTTGGGGGAACGCTCTCTTTCGGGGGGGGAGT
TCTCCCAATGGATGCCAACACAAACAAATATTTTTTTAAACTTATTCAATCAACACAAGATTT
CTTTTAATAGAAAACAACTTCAAAACTTTCAACAATGGATCTCTTGGTTCTCGCATCGATGAA
GAACGCAGCGAAATGCCGATACGTAATGTGAATTGCAGAATTCCGTGAATCATCGAATCTTTG
AACGCACATTGCGCCCTCTGGTATTCCGGGGGGCATGCCTGTTTGAGCGTCATTT SEQ ID NO: 25
Penicillium spp.
GGAAGTAAAAGTCGTAACAAGGTTTCTGTATTGTTGCTTCGGCGGGCCCGCCTTAACTGGCCG
CCGGGGGGCTTACGCCCCCGGGCCCGCGCCCGCCGAAGACACCCTCGAACTCTGTCTGAAGAT
TGTAGTCTGAGTGAAAATATAAATTATTTAAAACTTTCAACAACGGATCTCTTGGTTCCGGCA
TCGATGAAGAACGCAGCGAAATGCGATACGTAATGTGAATTGCAAATTCAGTGAATCATCGAG
TCTTTGAACGCACATTGCGCCCCCTGGTATTCCGGGGGGCATGCCTGTCCGAGCGTCATTGCT
GCCCTCAAGCACGGCTTGTGTGTTGGGCCCCCGTCCTCCCGATCCCGGGGGACGGCCCCCGAA
AAGGCAGCGGCGGCACCGCCTTCCCGGTCCTCCGAGCCTTATGGGGCTTTGTTCACCCCGCTC
TTGTTAGGCCCCGGCCCGCCTGCCCCCGATCAACCCAAATTTTTATCCAAGTTTGACCTCCGG
ATCANGTTAGGGATAC SEQ ID NO: 26
Malbranchia spp.
GGAAGTAAAAGTCGTAACAAGGTTTCTGTAGGTGAACCTGCAGAAGGATCATTAGTGAAAGCA
AGGGCCAGCCATACGGACGGCGCTACTCGCGTACAACGTCTCTGGCGTCCGTAGGTGAACCTG
CGGAAGGATCATTAAAGTGTTAAGCCGGCGCCTCCGTGTGCCGGTGAAACTCCACCCTTGACT
ACTATACCACATGTTGCTTTGGCGGGCCCGCCTCCGGGCCGCCGGGGGCCCTGCCCCTGGCCC
GCGCCCGCCAGAGATACACTGAACCCTTTGTGAAATTGGACGTCTGAGTTGATGATCAATCAT
TAAAACTTTCAACAATGGATCTCTTGGTTCCGGCATCGATGAAGAACGCAGCGAAATGCGATA
AGTAATGTGAATTGCAGAATTCCGTGAATCATCGAATCTTTGAACGCACATTGCGCCCCCTGG
TATTCCGGGGGGCATGCCTGTCCGAGCGTCATTGCAACCCTCAAGCGCGGCTTGTGTGTTGGG
CCTCGTCCCCCGTGGACGTGCCCGAAAGGCAGTGGCGGCGTCCGTTTCGGTGCCCGAGCGTAT
GGGAACTCTTATACCGCTCGAAGGGCCCGGCGGCGCTGGTCAGAACCAAATCTTTTACCGGTT
GACCTCGGATCAGGTAGGGATACC SEQ ID NO: 27
Arthrogrothilus spp.
GGAAGTAAAAGTCGTAACAAGGTTTCTGTAGGTGAACCTGCAGAAGGATCATTAGTGAAAGCA
AGGGCCAGCCATACGGACGGCGCTACTCGCGTACAACGTCTCTGGCGTATGGTGTCTTGGTTG
TAGCTGGCTCCTCGGAGCATTGTGCACGCCCGCCATTTTTATCTATCCACCTGTGCACCGACT
GTAGGTCTGGATGACTCTCGTGCTCTCTGAGTGCGGATGCGAGGATTGCCCTCTTGAGGTGTC
TCTCCTCGAATTTCCAGGCTCTACGTCTTTTTACACACCCCACAAGTATGATATAGAATGTAG
TCAATGGGCTTGATCGCCTATAAAACACTATACAACTTTCAGCAACGGATCTCTTGGCTCTCG ADDENDUM 1-continued CATCGATGAAGAACGCAGCGAAATGCGATAAGTAATGTGAATTGCAGAATTCAGTGAATCATC
GAATCTTTGAACGCACCTTGCGCTCCTTGGTATTCCGAGGAGCATGCCTGTTTGAGTTGTCAT
TAAATTCTCAACCTCACCCCGTTTTCCCGAACGGTTCTCCGAGGCTTGGATGTGGGTTTTTGT
GCCAGGCTTGCCTCCAGCCGCGGTCTTGTCCCCTTGAAATTGCATTTAGCGAGTTCGTACTTG
AGCTCCGTCTATGGTNGTGATAAATTATCTACGCCCGTTGGACNGTTTAAAACTCCCTTCTA
ACCGTCCCGCAANGANAATANCTTTT
SEQ ID NO: 28
*Cylindrocarpon destructans*
GGAAGTAAAAGTCGTAACAAGGTTTCTGTAGGTGAACCTGCAGAAGGATCATTAGTGAAAGCA
AGGGCCAGCCATACGGACGGCGCTACTCGCGTACAACGTCTCTGGCGTCCGTAGGTGAACCTG
CGGAAGGATCATTACAGTGCCGCCGGGACGCGCCCCCTAAACCGGGGCGCCGAGTTTACAACT
CCCAAACCCCTGTGAACATACCATTTGTTGCCTCGGCGGTGCCTGCTTCGGCAGCCCGCCAGA
GGACCCAAACCCTTGATTTTATACAGTATCTTCTGAGTAAATGATTAAATAAATCAAAACTTT
CAACAACGGATCTCTTGGTTCTGGCATCGATGAAGAACGCAGCGAAATGCGATAAGTAATGTG
AATTGCAGAATTCAGTGAATCATCGAATCTTTGAACGCACATTGCGCCCGCCAGTATTCTGGC
GGGCATGCCTGTTCGAGCGTCATTTCAACCCTCAAGCCCCCGGGCTTGGTGTTGGAGATCGGC
GTGCCCCCCGGGGCGCGCCGGCTCCCAAATATAGTGGCGGTCTCGCTGTAGCTTCCTCTGCGT
AGTAGCACACCTCGCACTGGAAAACAGCGTGGCCACGCCGTTAAACCCCCCACTTCTGAAAGG
TTCTATTCTTCTTAGGTTGACCTCGGATCAGGTAGGGATACC
SEQ ID NO: 29
*Sporothrix schenkii*
GGAAGTAAAAGTCGTAACAAGGTTTCTGTAGGTGAACCTGCAGAAGGATCATTAGTGAAAGCA
AGGGCCAGCCATACGGACGGCGCTACTCGCGTACAACGTCTCTGGCGGTCGTAACAAGGTCTC
CGTTGGTGAACCAGCGGAGGGATCATTACAGAGTTTTCACAACTCCCAACCCTTGCGAACCGT
ACCCAATCTCGTTCTCGTTGCTTCTGGCGGGGGGAANCGGGGGGGCGCCCNACACGGCCCCCT
CTTGCCCCCGCCCGCCAGGGGCGGCGGGCCCTACGAACCTTTGTATCTCAACCACTAGAAAAC
CGTCTGAGGAAAAAACAAAATAATCAAAACTTTCAACAACGGATCTCTTGGCTCTGGCATCGA
TGAAGAACGCAGCGAAATGCGATACGTAATGTGAATTGCAGAATTCAGCGAACCATCGAATCT
TTGAACGCACATTGCGCCCGCCAGCATTCTGGCGGGCATGCCTGTCCGAGCGTCATTTCCCCC
CTCACGCGCCCCGTTGCGCGCTGGTGTTGGGGCGCCCTCCGCCTGGCGGGGGGCCCCCGAAAN
CGAGTGGCGGGCCCTGTGGAAGGCTCCGAGCGCAGTACCGAACGCATGTTCTCCCCTCGCTCC
GGACGCCCCCCAGGCGCCCTGCCGTGAAAACGCGCATGACGCGCAGCTCTTTTTACAAGGTTG
ACCTCGCCGCTGACCTCGGATCAGTAGGGAATAC
SEQ ID NO: 30
*Penicillium marnefeii*
GGAAGTAAAAGTCGTAACAAGGTTTCTGTAGGTGAACCTGCAGAAGGATCATTAGTGAAAGCA
AGGGCCAGCCATACGGACGGCGCTACTCGCGTACAACGTCTCTGGCGTCCGTAGGTGAACCTG
CGGAAGGATCATTACCGAGTGAGGGCCCTCTGGGTCCAACCTCCCACCCGTGTCTATCGTACC
TTGTTGCTTCGGCGGGCCCGCCGTTTCGACGGCCACCGGGGAGGCCTTGCGCCCCCGGGCCCG
CGCCCGCCGAAGACCCCAACATGAACGCTGTTCTGAAAGTATGCAGTCTGAGTTGATTATCGT
AATCAGTTAAAACTTTCAACAACGGATCTCTTGGTTCCGGCATCGATGAAGAACGCAGCGAAA
TGCGATAAGTAATGTGAATTGCAGAATTCAGTGAATCATCGAGTCTTTGAACGCACATTGCGC
CCCCTGGTATTCCGGGGGGCATGCCTGTCCGAGCGTCATTGCTGCCCTCAAGCACGGCTTGTG
TGTGGGCCCCCGTCCCCCTCTCCCGGGGGACGGGCCCGAAAGGCAGCGGCGGCACCGCGTCCG
GTCCTCGAGCGTATGGGGCTTTGTCACCTGCTCTGTAGGCCCGGCCGGCGCCAGCCGACACCC
AACTTTATTTTTCTAAGGTTGACCTTGGATCAGGTAGGGATACCCGCTGCCTCGGATCAGGTA
GGAATAC
SEQ ID NO: 31
*Coccidiodes immitis*
GGAAGTAAAAGTCGTAACAAGGTTTCTGTAGGTGAACCTGCAGAAGGATCATTAGTGAAAGCA
AGGGCCAGCCATACGGACGGCGCTACTCGCGTACAACGTCTCTGGCGTCCGTAGGTGCGTCCG
GCTGCGCACCTCCCCCGCGGGGGTTCGCGCGGTCCGTACCTCCCACCCGTGTTTACTGAACCA
TTGTTGCCTTGGCAGGCCTGCCGGGCCTCCGGCTGCCGGGGATCGCCCGCCTTGCGCGGCGTC
CCGGGCGCGCGCCTGCCAGCGGATCAATTGAACTCTTATGTGAAGATTGTCAGTCTGAGCATC
ATAGCAAAAATCAAACAAAACTTTCAACAACGGATCTCTTGGTTCCGGCATCGATGAAGAACG
CAGCGAAATGCGATAAGTAATGTGAATTGCAGAATTCCGTGAATCATCGAATCTTTGAACGCA
CATTGCGCCCTCTGGTATTCCGGGGGGCATGCCTGTTCGAGCGTCATTGCAAACCCTTCAAGC
ACGGCTTGTGTGTTGGGCCAACGTCCCCGCTTGTGTGGACGGGCCTGAAATGCAGTGGCGGCA
CCGAGTTCCTGGTGTCTGAGTGTATGGGAAATCACTTCATCGCTCAAAGACCCGATCGGGGCC
GATCTCTTTTTTTTATTATATCCGGTTTGACCTCGGATCAGGTAGGAGTACCCGCTGAACTTA
CCTCGGATCAGGTAGGAATAC
SEQ ID NO: 32
*Candida tropicalis*
GGAAGTAAAAAGTCGTAACAAGGTTTCCGAGGNGAACCTGCGGAAGGATCNTTACTGATTTGC
TTAANTGCCCCNCATGNGTTTTTTATTNAACAAATTTNTTTGGNGGCGGGANCAATCCNACCN
CCANAGGTTANAACTAAACCNAACTTTTTNTTTACAGTCNAACTTNATTTATTATTACNANAG
TCAAAACTTTCAACAACGGATNTNTTGGNTNTNGCATCNATGAANAACNCANCNAAATNCNAT
ACGTAATATNAATTGCANANATTNGTNAATCATCGAATCTTTNAACGCCCNNTGCNCCCTTTG
GTATTCCAAANGGCANGCCTGTTTNANCGTCATTTNTCCCNCNAACCCCCGGGNTTGGTGTTN
AACNANACCCNAGGTTTGTTTGAAAAAATTTAACGTGGAAACTTATTTTAAACGACTTAGGTT
TATCCNAAAACGCTTATTTTGCTAGGGCCACCACAATTTATTTCAAACTTGACCCA
SEQ ID NO: 33
*Candida parapsilosis*
GGAAGTAAAAAGTCGGTAACAAGGTTTCCGTAGGTGAACCTGCGGAAGGATCATTACAGAATG
AAAAGTGCTTAACTGCATTTTTTCTTACACATGTGTTTTTCTTTTTTTGAAAACTTTGCTTTG
GTAGGCCTTCTATATGGGGCCTGCCAGAGATTAAACTCAACCAAATTTTATTTAATGTCANCC ADDENDUM 1-continued

```
GATTATTTAATAGTCAAAACTTTCAACAACGGATCTCTTGGTTCTCGCATCGATGAAGAACGC
AGCGAAATGCGATAAGTAATATGAATTGCAGATATTCGTGAATCATCGAATCTTTGAACGCNC
ATTGCGCCCTTTGGTATTCCAAAGGGCATGCCTGTTTGAGCGTCATTTCTCCCNCAAACCCTC
GGGTTTGGTGTTGAGCGATACGCTGGGTTTGCTTGAAAGAAAGGCGGAGTATAAACTAATGGA
TAGGTTTTTTCCACTCATTGGTACAAACTCCAAAACTTCTTCCAAATTCGACCCA
```

Refernces

1. Altschul, S. F., T. L. Madden, A. A. Schaffer, J. Zhang, Z. Zhang, W. Miller, and D. J. Lipman. 1997. Gapped BLAST and PSI-BLAST: a new generation of protein database search programs. Nuc Acid Res. 25:33389–3402.
2. Beck-Sague, C., and W. R. Jarvis. 1993. Secular trends in the epidemiology of nosocomial fungal infections in the United States, 1980–1990. National Nosocomial Infections Surveillance System. J Infect Dis. 167:1247–51.
3. Bretagne, S., J. M. Costa, A. Mazmorat-Khuong, F. Poron, C. Cordonnier, M. Vidaud, and J. Fleury-Feith. 1995. Detection of Aspergillus species DNA in bronchoalveolar lavage samples by competitive PCR. J Clin Microbiol. 33:1164–8.
4. Denning, D. 1998. Invasive aspergillosis. Clin Infect Dis. 26:781–805.
5. Denning, D. W. 1996. Therapeutic outcome in invasive aspergillosis. Clin Infect Dis. 23:608–615.
6. Einsiel, H., H. Hebart, G. Roller, J. Loffler, I. Rothenhofer, C. A. Muller, R. A. Bowden, J. van Burik, D. Engelhard, L. Kanz, and U. Schumacher. 1997. Detection and identification of fungal pathogens in blood by using molecular probes. J Clin Microbiol. 35:1353–1360.
7. Gaskell, G. J., D. A. Carter, W. J. Britton, E. R. Tovey, F. H. Benyon, and U. Lovborg. 1997. Analysis of the internal transcribed spacer regions of ribosomal DNA in common airborne allergenic fungi. Electrophoresis. 18:1567–9.
8. Groll, A., P. Shah, C. Mentzel, M. Schneider, and G. Just-Neubling. 1996. Trends in the postmortem epidemiology of invasive fungal infections at a university hospital. J Infect. 33:23–32.
9. Guarro, J., J. Gene, and A. M. Stchigel. 1999. Developments in fungal taxonomy. Clin Microbiol Rev. 12:454–500.
10. Iwen, P., M. Rupp, A. Languas, E. Reed, and S. Hinrichs. 1998. Invasive pulmonary aspergillosis due to *Aspergillus terreus:* 12-year experience and review of the literature. Clin Infect Dis. 26:1092–1097.
11. Lee, C. H., J. Helweg-Larsen, X. Tang, S. Jin, B. Li, M. S. Bartlett, J. J. Lu, B. Lundgren, J. D. Lundgren, M. Olsson, S. B. Lucas, P. Roux, A. Cargnel, C. Atzori, O. Matos, and J. W. Smith. 1998. Update on *Pneumocystis carinii* f. sp. hominis typing based on nucleotide sequence variations in internal transcribed spacer regions of rRNA genes. J Clin Microbiol. 36:734–41.
12. Melchers, W. J., P. E. Verweij, P. van den Hurk, A. van Belkum, B. E. De Pauw, J. A. Hoogkamp-Korstanje, and J. F. Meis. 1994. General primer-mediated PCR for detection of Aspergillus species. J Clin Microbiol. 32:1710–7.
13. Mitchell, T. G., T. J. White, and J. W. Taylor. 1992. Comparison of 5.8S ribosomal DNA sequences among the basidiomycetous yeast genera Cystofilobasidium, Filobasidium and Filobasidiella. J Med Vet Mycol. 30:207–18.
14. Moore, C. B., D. Law, and D. W. Denning. 1993. In-vitro activity of the new triazole D0870 compared with amphotericin B and itraconazole against Aspergillus spp. J Antimicrob Chemother. 32:831–6.
15. Nucci, M., N. Spector, A. P. Bueno, C. Solza, T. Perecmanis, P. C. Bacha, and W. Pulcheri. 1997. Risk factors and attributable mortality associated with superinfections in neutropenic patients with cancer. Clin Infect Dis. 24:575–9.
16. Oakley, K. L., C. B. Moore, and D. W. Denning. 1997. In vitro activity of SCH-56592 and comparison with activities of amphotericin B and itraconazole against Aspergillus spp. Antimicrob Agents Chemother. 41:1124–6.
17. Rath, P. 1998. Susceptibility of Aspergillus strains from culture collections to amphotericin B and itraconazole. J Antimicrob Chemo. 41:567–570.
18. Sampson, R. A. 1994. Current systematics of the genus Aspergillus. In K. A. Powell and A. Renwick and J. F. Peberdy (ed.), The Genus Aspergillus. From taxonomy and genetics to industrial application. Plenum Press, New York. p. 261–276.
19. Shin, J. H., F. S. Nolte, B. P. Holloway, and C. J. Morrison. 1999. Rapid identification of up to three Candida species in a single reaction tube by a 5' exonuclease assay using fluorescent DNA probes. J Clin Microbiol. 37:165–70.
20. Shin, J. H., F. S. Nolte, and C. J. Morrison. 1997. Rapid identification of Candida species in blood cultures by a clinically useful PCR method. J Clin Microbiol. 35:1454–9.
21. Sugita, T., A. Nishikawa, R. Ikeda, and T. Shinoda. 1999. Identification of medically relevant Trichosporon species based on sequences of internal transcribed spacer regions and construction of a database for Trichosporon identification. J Clin Microbiol. 37:1985–93.
22. Sutton, D., S. Sanche, S. Revankar, A. Fothergill, and M. Rinaldi. 1999. In vitro amphotericin B resistance in clinical isolates of *Aspergillus terreus*, with a head-to-head comparison to voriconazole. J Clin Microbiol. 37:2343–2345.
23. Tureene, C. Y., S. E. Sanche, D. J. Hoban, J. A. Karlowsky, and A. M. Kabani. 1999. Rapid identification of fungi by using the ITS2 genetic region and an automated fluorescent capillary electrophoresis system. J Clin Microbiol. 37:1846–51.
24. Van Burik, J., D. Myerson, R. Schreckhise, and R. Bowen. 1998. Panfungal PCR assay for detection of fungal infection inhuman blood specimens. J Clin Microbiol. 36:1169–1175.
25. von Eiff, M., N. Roos, R. Schulten, M. Hesse, M. Zuhlsdorf, and J. van de Loo. 1995. Pulmonary aspergillosis: early diagnosis improves survival. Respiration. 62:341–7.
26. White, T., T. Burns, S. Lee, and J. Taylor. 1990. Amplification and direct sequencing of fungal ribosomal RNA genes for phylogenetics. In M. A. Innis, D. H. Gelfand, J. J. Sninsky, and T. J. White (ed.), PCR protocols. A guide to methods and applications. Academic Press, Inc., San Diego, Calif.:315–322.

27. Yamakami, Y., A. Hashimoto, I. Tokimatsu, and M. Nasu. 1996. PCR detection of DNA specific for Aspergillus species in serum of patients with invasive aspergillosis. J Clin Microbiol. 34:2464–8.

28. Yamakami, Y., A. Hashimoto, B. Yamagata, P. Kamberi, R. Karashima, H. Nagai, and M. Nasu. 1998. Evaluation of PCR for detection of DNA specific for Aspergillus species in sera of patients with various forms of pulmonary aspergillosis. J. Clin Microbibl 36:3619–23

29. Sambrook et al. *Molecular Cloning*, Cold Spring Harbor Laboratory (1989)

30. Henry T., P. C. Iwen, and S. H. Hinrichs. 2000. Identification of Aspergillus species using internal transcribed spacer regions 1 and 2. J. Clin Microbiol. 38:1510–1515.

31. Iwen, P. C., L. Sigler, S. Tarantolo, D. A. Sutton, M. G. Rinaldi, R. P. Lackner, D. I. McCarthy, and S. H. Hinrichs. 2000 Pulmonary infection caused by *Gymnascella hyalinospora* in a patient with acute myelogenous leukemia. J. Clin. Microbiol. 38: 375–381.

32. Iwen, P. C., S. Tarantolo, D. A. Sutton, M. G. Rinaldi, and S. H. Hinrichs. 2000. Cutaneous infection caused by *Cylindrocarpon lichenicola* in a patient with acute myelogenous leukemia. J. Clin. Microbiol. (in second revision)

33. Iwen, P. C., T. Henry, A. R. Lodes, and S. H. Hinrichs. 2000. Culture identification of *Histoplasma capsulatum* using the rDNA internal transcribed spacer regions 1 and 2 as a molecular target. $100^{th}$ General Meeting of the American Society for Microbiology, Los Angeles, Calif., Abstract F-57.

34. Shearon, E. C., S. H. Hinrichs, D. A. Sutton, M. G. Rinaldi, D. L. McCarthy, D. L. Sudan, and P. C. Iwen. 2000. Correlation of susceptibility testing with clinical response in patients without hematologic malignancies who develop candidemia caused by *Candida lusitaniae.* $100^{th}$ General Meeting of the American Society for Microbiology, Los Angeles, Calif., While preferred embodiments of the present invention have been described and specifically exemplified above, it is not intended that the invention be limited to such embodiments. Various modifications may be made thereto without departing from the scope and spirit of the present invention, as set forth in the following claims.

---

What is claim is:

1. A method of determing whether one or more fungal Asperillus species is present in a sample of fungi, said method comprising the follong steps:

a) extracting nucleic acid matcrial from fungi contained in a patient sample from a patient suspected of having an Aspergillus infection;

b) adding two oligonucleotide primers, one of said primers consisting of SEQ ID: NO:1. and the other primer consisting of SEQ ID NO:2. said primers bracketing a hypervariable region on the rRNA present in the fungal species of said group, and said primers being capable of amplifying *Aspergillus Ustus* (SEQ ID NO: 3) *Aspergillus terreus* (SEO ID NO: 4), *Aspergillus niger* (SEQ ID No: 5), *Aspergillus nigulans* (SEQ ID No: 6), *Aspergillus fumigatus* (SEQ ID NO: 7), and *Aspergillus flavus* (SEQ ID NO: 8);

c) amplifying the sequence between said primers; and d) using one or more detectably labeled probes directed to a portion of the hypervariable region braketed by sad primers, said probes beg selected from the group consisting of at least 15–25 contiguous nucleotides ot SEQ ID NO: 3, SEQ ID NO: 4, SEQ ID NO: 5, SEQ ID NO: 6, SEQ ID NO: 7 and SEQ ID NO: 8 which distinguish said species, each said labeled probe being specific for one of asid fungal species from said group, to determine whsether said fungal species identified by each said labeled probe is present in said sample.

2. The method of claim 1, wherein said amplifying procedure in tht polymerase reaction.

3. The method of claim 1 in which said one or more probes hybridize to a nucleic acid sequence encoding the internal spacer regions of a pathogenic Aspergillus species gene sequence and is selected from the group consisting of (SEQ ID NO:3), (SEQ ID NO:4), (SEQ ID NO:5), (SEQ ID NO:6), (SEQ ID NO:7), and (SEQ ID NO:8).

4. The method of claim 1 wherein, in step (d), more than one probe is used, each said probe being connected to (a) a different signal moiety or (b) a moiety which allows sepration of aid probes.

5. A method for determining which Aspergillus species selected from the group consisting of *Aspergillus ustus* (SEQ ID NO: 3), *Apergillus terreus* (SEQ ID NO: 4), *Aspergillus miger* (SEQ ID NO: 5), *Asporgillus nidulans* (SEQ ID NO: 6), *Aspergillus fumigatus* (SEQ ID NO: 7), and *Aspergillus flavus* (SEQ ID NO: 8) is present in a biological sample, said method comprising comparing the sequences of fungal nucleic acid extracted from said biological sample with the nucleic acid sequences of SEQ ID NOS: 3–8 to determine which pathogenic Aspergillus species is present in said biological sample, each of said sequences of SEQ ID NOs: 3–8 being amplified by polymerase chain reaction using a primer set consisting of SEQ ID NOs: 1 and 2.

6. A method for determining which Aspergillus species is present in a biological sample, said species being selected from the group consisting of *Aspergillus ustus* (SEQ ID NO: 3), *Aspergillus terreus* (SEQ ID NO: 4), *Aspegillus niger* (SEQ ID NO; 5), *Aspergillus nidulans* (SEQ ID NO: 6), *Aspergillus fumigatus* (SEQ MD NO: 7), and *Aspergillus flavus* (SEQ ID NO: 8), comprising the step of:

a) extracting fungal nucleic acid from said biological sample and fungal nucleic acid with polymerase chain reaction using a primer set consisting of SEQ ID: NO: 1 and 2;

b) generating restriction mapping patterns of said fungal nucleic acid; and c) comparimg said restriction mapping patterns of said fungal nucleic acid to the restriction mapping patterns of the nucleic acid sequences of SEQ ID NOs: 3–8, wherein identical restriction mapping patterns are indicative of which Aspergillus species is present in said biological sample.

7. A method for determining which *Aspeillus species selected from the group consisting of Aspergillus ustus* (SEQ ID NO: 3), *Aspergillus terreus* (SEQ ID NO: 4), *Aspergillus niger* (SEQ ID NO: 5), *Aspergillus nidulans* (SEQ ID NO: 6), *Aspergillus fumigatus* (SEQ ID NO: 7), and *Aspergillus flavus* (SEQ ID NO. 8) is present in a biological sample, said method compising the steps of:

a) obtaining permeabilized tissue sections containing fungal nucleic acid from a patient;

b) contacting said permeabilized tissue section with fluorescent molecular probes specific for pathogenic Aspergillus species comprising the sequence of SEQ ID No: 3–85; and c) analysing said permeabilizd tissue sections with said fluorescent molecular probes, the detection of which is indicative of the presence of pathogenic Aspergillus species in said biological sample.

8. A universal primrer set for amplification of a target DNA sequence associated with pathogenic strains of fungi, said primer set consisting of the following sequence: GGAAGTAAAAGTCGTAACAAGG (SEQ ID NO: 1) and GTATCCCTACCTGATCCGAGG (SEQ ID NO, 2).

9. A kit for identifying pathogenic fungal species in a biological sample, said kit comprising:

a) a universal primer set, said primer set consisting of th sequenee of SEQ ID NO. 1 and SEQ ID NO: 2;

b) lysis buffer suitable for lysing fungus in said biological sample, such that DNA is released from said fungus upon exposure to said buffer;

c) a polymerase enzyme suitable for use in polymerase chain reaction;

d) means for contacting said researh DNA with a primer set consisting of the sequence of SEQ ID NO: 1 and NO: 2 under conditions where amplification of pathogenicity-associated ITS sequence occurs, if said pathogenic fungus is present in said sample; and e) means for detecting said amplified sequence, if present.

10. A kit as claimed in claim 9, further comprising a detectable label, for detecting said amplified sequence.

11. A kit as claimed in claim 9, further comprising a gel apparatus for performing gel electrophoresic of said amplified sequence.

12. A kit a claimed in claim 9, further comprising nucleic acids having sequences of SEQ ID NOs: 3–10.

* * * * *

UNITED STATES PATENT AND TRADEMARK OFFICE

CERTIFICATE OF CORRECTION

PATENT NO. : 6,872,523 B1

APPLICATION NO. : 09/580797
DATED : March 29, 2005
INVENTOR(S) : Peter C. Iwen, Steven H. Hinrichs and Travis Henry It is certified that error appears in the above-identified patent and that said Letters Patent is hereby corrected as shown below:

Column 1, line 52: with invasive disease. Early recognition of invasive fungal
Column 2, line 48: Aspergillus fumigatus, Aspergillus flavus, Pseudallescheria
Column 2, line 61: tained in the sample; b) adding two known oligonucleotide
Column 3, line 18: probes are used in step (d each being connection to (a) a
Column 3, line 24: Penicillium spp., having the nucleotide sequence of (SEQ
Column 3, line 63: is separated from sequences with which it is immediately
Column 3, line 64: contiguous (in the 5' and 3' directions) in the naturally
Column 4, line 42: homology is set forth below (Sambrook et al., Molecular
Column 5, line 38: or similar activity to yield a primer extension product. The
Column 5, line 44: plate to prime the synthesis of the desired extension
Column 5, line 45: product, that is, to be able to anneal with the desired template
Column 5, line 50: an exact complement of the desired template. For example,
Column 6, line 46: I. Preparation of Nucleic Acid Molecules and Primers
Column 6, line 64: Inc., Valencia, CA) and protocols for crude cell lysates as
Column 7, line 16: used according to methods known in the art, such as the
Column 7, line 17: polymerase chain reaction (PCR) method.
Column 7, line 22: In accordance with the present invention, nucleic acid
Column 7, line 40: cDNA, genomic DNA, RNA, and fragments thereof which
Column 8, line 11: fungi is DNA sequence analysis, however, the methodology
Column 8, line 27: either the pathogenic nucleic acid sequence, the
Column 8, line 40: e) using PCR involving one or more primer-based
Column 9, line 68: et al. were made to optimize the amplification procedure
Column 10, line 26: purified and ligated into the PCR 2.1 plasmid vector using
Column 10, line 28: Diego, CA. Compentent INV F' One Shot cells were
Column 11, line 5: Sequence Analysis
Column 11, line 36: Sequence Analysis of Aspergillus specimens was per-
Column 12, line 15 of text under table: that both single nucleotide differences and short lengths of
Column 15, line 60: Abbreviations: ATCC, American Type Culture Collection; IMI, Invasive Mold Infections (UMNC); a As compared to A. fumigatus ATCC 36607. b Sequence deposited into GenBank as part of this study. C Reference strain sequenced but not deposited into GenBank.
Column 16, line 11: infectious molds from clinical samples. The number of cases
Column 16, line 60: 1 and 2 regions (21). Gaskell et al. investigated sequence
Column 18, line 24: results available within 48 h, confirmed the value of this
Column 18, line 63: facilitates the species specific identification of fungi. Addi-
Column 29, line 1 of text following addendum 1: References

UNITED STATES PATENT AND TRADEMARK OFFICE
CERTIFICATE OF CORRECTION

PATENT NO. : 6,872,523 B1
APPLICATION NO. : 09/580797
DATED : March 29, 2005
INVENTOR(S) : Peter C. Iwen, Steven H. Hinrichs and Travis Henry It is certified that error appears in the above-identified patent and that said Letters Patent is hereby corrected as shown below:

Column 61, line 1: What is claimed is:
Column 61, line 4: method comprising the following steps:
Column 61, line 5: a) extracting nucleic acid material from fungi contained in
Column 61, line 9: ers consisting of SEQ ID NO:1 and the other primer
Column 61, line 10: consisting of SEQ ID NO:2, said primers bracketing a
Column 61, line 14: Aspergillus terrus (SEQ ID NO:4), Aspergillus niger
Column 61, line 15: (SEQ ID NO:5), Aspergillus nigulans (SEQ ID NO:6),
Column 61, line 20: a portion of the hypervariable region bracketed by said
Column 61, line 21: primers, said probes being selected from the group con-
Column 61, line 22: sisting of at least 15-25 contiguous nucleotides of SEQ
Column 61, line 26: one of said fungal species from said group, to deter-
Column 61, line 27: mine whether said fungal species identified by each
Column 61, line 30: procedure in the polymerase chain reaction.
Column 61, line 39: different signal moiety or (b) a moiety which allows separ-
Column 61, line 40: ation of said probes.
Column 61, line 49: nucleic acid sequences of SEQ ID NOs: 3-8 to determine
Column 61, line 58: (SEQ ID NO: 5), Aspergillus nidulans (SEQ ID NO: 6),
Column 61, line 59: Aspergillus fumigatus (SEQ ID NO: 7), and Aspergillus
Column 61, line 60: flavus (SEQ ID NO: 8), said method comprising the step of:
Column 62, line 2: sample and amplifying said fungal nucleic acid with polymerase chain
Column 62, line 3: reaction using a primer set consisting of SEQ ID NO:
Column 62, line 7: c) comparing said restriction mapping patterns of said
Column 62, line 13: 7. A method for determining which Aspergillus species
Column 62, line 18: flavus (SEQ ID NO: 8), is present in a biological sample, said
Column 62, line 25: ID NOs: 3-8; and
Column 62, line 26: c) analyzing said permeabilized tissue sections with said
Column 62, line 30: 8. A universal primer set for amplification of a target
Column 62, line 34: GTATCCCTACCTGATCCGAGG (SEQ ID NO: 2).
Column 62, line 37: a) a universal primer set, said primer set consisting of the
Column 62, line 38: sequence of SEQ ID NO: 1 and SEQ ID NO: 2;
Column 62, line 44: d) means for contacting said released DNA with a primer
Column 62, line 53: apparatus for performing gel electrophoresis of said ampli-
Column 62, line 55: 12. A kit as claimed in claim 9, further comprising nucleic

UNITED STATES PATENT AND TRADEMARK OFFICE

CERTIFICATE OF CORRECTION

PATENT NO. : 6,872,523 B1
APPLICATION NO. : 09/580797
DATED : March 29, 2005
INVENTOR(S) : Peter C. Iwen, Steven H. Hinrichs and Travis Henry It is certified that error appears in the above-identified patent and that said Letters Patent is hereby corrected as shown below:

Column 62, line 56: acids having sequences of SEQ ID NOs: 3-8.

Signed and Sealed this

Eighth Day of August, 2006

JON W. DUDAS
*Director of the United States Patent and Trademark Office*

UNITED STATES PATENT AND TRADEMARK OFFICE

CERTIFICATE OF CORRECTION

PATENT NO. : 6,872,523 B1
APPLICATION NO. : 09/580797
DATED : March 29, 2005
INVENTOR(S) : Peter C. Iwen, Steven H. Hinrichs and Travis Henry It is certified that error appears in the above-identified patent and that said Letters Patent is hereby corrected as shown below:

Column 1, line 52: with invasive disease. Early recognition of invasive fungal
Column 2, line 48: Aspergillus fumigatus, Aspergillus flavus, Pseudallescheria
Column 2, line 61: tained in the sample; b) adding two known oligonucleotide
Column 3, line 18: probes are used in step (d each being connection to (a) a
Column 3, line 24: Penicillium spp., having the nucleotide sequence of (SEQ
Column 3, line 63: is separated from sequences with which it is immediately
Column 3, line 64: contiguous (in the 5' and 3' directions) in the naturally
Column 4, line 42: homology is set forth below (Sambrook et al., Molecular
Column 5, line 38: or similar activity to yield a primer extension product. The
Column 5, line 44: plate to prime the synthesis of the desired extension
Column 5, line 45: product, that is, to be able to anneal with the desired template
Column 5, line 50: an exact complement of the desired template. For example,
Column 6, line 46: I. Preparation of Nucleic Acid Molecules and Primers
Column 6, line 64: Inc., Valencia, CA) and protocols for crude cell lysates as
Column 7, line 16: used according to methods known in the art, such as the
Column 7, line 17: polymerase chain reaction (PCR) method.
Column 7, line 22: In accordance with the present invention, nucleic acid
Column 7, line 40: cDNA, genomic DNA, RNA, and fragments thereof which
Column 8, line 11: fungi is DNA sequence analysis, however, the methodology
Column 8, line 27: either the pathogenic nucleic acid sequence, the
Column 8, line 40: e) using PCR involving one or more primer-based
Column 9, line 68: et al. were made to optimize the amplification procedure
Column 10, line 26: purified and ligated into the PCR 2.1 plasmid vector using
Column 10, line 28: Diego, CA. Competent INV F' One Shot cells were
Column 11, line 5: Sequence Analysis
Column 11, line 36: Sequence Analysis of Aspergillus specimens was per-
Column 12, line 15 of text under table: that both single nucleotide differences and short lengths of
Column 15, line 60: Abbreviations: ATCC, American Type Culture Collection; IMI, Invasive Mold Infections (UMNC); a As compared to A. fumigatus ATCC 36607. b Sequence deposited into GenBank as part of this study. C Reference strain sequenced but not deposited into GenBank.
Column 16, line 11: infectious molds from clinical samples. The number of cases
Column 16, line 60: 1 and 2 regions (21). Gaskell et al. investigated sequence
Column 18, line 24: results available within 48 h, confirmed the value of this
Column 18, line 63: facilitates the species specific identification of fungi. Addi-
Column 29, line 1 of text following addendum 1: References

UNITED STATES PATENT AND TRADEMARK OFFICE

CERTIFICATE OF CORRECTION

PATENT NO. : 6,872,523 B1
APPLICATION NO. : 09/580797
DATED : March 29, 2005
INVENTOR(S) : Peter C. Iwen, Steven H. Hinrichs and Travis Henry It is certified that error appears in the above-identified patent and that said Letters Patent is hereby corrected as shown below:

Column 61, line 1: What is claimed is:
Column 61, line 4: method comprising the following steps:
Column 61, line 5: a) extracting nucleic acid material from fungi contained in
Column 61, line 9: ers consisting of SEQ ID NO:1 and the other primer
Column 61, line 10: consisting of SEQ ID NO:2, said primers bracketing a
Column 61, line 14: Aspergillus terreus (SEQ ID NO:4), Aspergillus niger
Column 61, line 15: (SEQ ID NO:5), Aspergillus nigulans (SEQ ID NO:6),
Column 61, line 20: a portion of the hypervariable region bracketed by said
Column 61, line 21: primers, said probes being selected from the group con-
Column 61, line 22: sisting of at least 15-25 contiguous nucleotides of SEQ
Column 61, line 26: one of said fungal species from said group, to deter-
Column 61, line 27: mine whether said fungal species identified by each
Column 61, line 30: procedure in the polymerase chain reaction.
Column 61, line 39: different signal moiety or (b) a moiety which allows separ-
Column 61, line 40: ation of said probes.
Column 61, line 49: nucleic acid sequences of SEQ ID NOs: 3-8 to determine
Column 61, line 58: (SEQ ID NO: 5), Aspergillus nidulans (SEQ ID NO: 6),
Column 61, line 59: Aspergillus fumigatus (SEQ ID NO: 7), and Aspergillus
Column 61, line 60: flavus (SEQ ID NO: 8), said method comprising the step of:
Column 62, line 2: sample and amplifying said fungal nucleic acid with polymerase chain
Column 62, line 3: reaction using a primer set consisting of SEQ ID NO:
Column 62, line 7: c) comparing said restriction mapping patterns of said
Column 62, line 13: 7. A method for determining which Aspergillus species
Column 62, line 18: flavus (SEQ ID NO: 8), is present in a biological sample, said
Column 62, line 25: ID NOs: 3-8; and
Column 62, line 26: c) analyzing said permeabilized tissue sections with said
Column 62, line 30: 8. A universal primer set for amplification of a target
Column 62, line 34: GTATCCCTACCTGATCCGAGG (SEQ ID NO: 2).
Column 62, line 37: a) a universal primer set, said primer set consisting of the
Column 62, line 38: sequence of SEQ ID NO: 1 and SEQ ID NO: 2;
Column 62, line 44: d) means for contacting said released DNA with a primer
Column 62, line 53: apparatus for performing gel electrophoresis of said ampli-
Column 62, line 55: 12. A kit as claimed in claim 9, further comprising nucleic

UNITED STATES PATENT AND TRADEMARK OFFICE

CERTIFICATE OF CORRECTION

PATENT NO. : 6,872,523 B1
APPLICATION NO. : 09/580797
DATED : March 29, 2005
INVENTOR(S) : Peter C. Iwen, Steven H. Hinrichs and Travis Henry It is certified that error appears in the above-identified patent and that said Letters Patent is hereby corrected as shown below:

Column 62, line 56: acids having sequences of SEQ ID NOs: 3-8.

This certificate supersedes Certificate of Correction issued August 8, 2006.

Signed and Sealed this

Twenty-fourth Day of October, 2006

JON W. DUDAS
*Director of the United States Patent and Trademark Office*

SEQUENCE LISTING

```
<160> NUMBER OF SEQ ID NOS: 39

<210> SEQ ID NO 1
<211> LENGTH: 22
<212> TYPE: DNA
<213> ORGANISM: Artificial Sequence
<220> FEATURE:
<223> OTHER INFORMATION: Primer

<400> SEQUENCE: 1

ggaagtaaaa gtcgtaacaa gg                                              22


<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2

gtatccctac ctgatccgag g                                               21


<210> SEQ ID NO 3
<211> LENGTH: 646
<212> TYPE: DNA
<213> ORGANISM: Aspergillus ustus

<400> SEQUENCE: 3

ggaagtaaaa gtcgtaacaa ggtttctgta ggtgaacctg cagaaggatc attagtgaaa      60

gcaagggcca gccatacgga cggcgctact cgcgtacaac gtctctggcg tccgtaggtg     120

aacctgcgga aggatcatta ccgagtgcag gtctgccccg ggcaggccta acctcccacc     180

cgtgaatacc tgaccaacgt tgcttcggcg gtgcgcccct ccgggggtag ccgccggaga     240

ccacaccgaa cctcctgtct ttagtgttgt ctgagcttga tagcaaacct attaaaactt     300

tcaacaatgg atctcttggt tccggcatcg atgaagaacg cagcgaactg cgataagtaa     360

tgtgaattgc agaattcagt gaatcatcga gtctttgaac gcacattgcg ccccctggca     420

ttccgggggg catgcctgtc cgagcgtcat tgctgccctt caagcccggc ttgtgtgttg     480
```

-continued

```
ggtcgtcgtc cctccgggg gacgggcccg aaaggcagcg gcggcaccgc gtccggtcct    540

cgagcgtatg gggctttgtc acccgctcga ttagggccgg ccgggcgcca gccggcgtct    600

ccaacctttt attttaccag gttgacctcg gatcaggtag ggatac                  646
```

<210> SEQ ID NO 4
<211> LENGTH: 685
<212> TYPE: DNA
<213> ORGANISM: Aspergillus terreus

<400> SEQUENCE: 4

```
ggaagtaaaa gtcgtaacaa ggtttctgta ggtgaacctg cagaaggatc attagtgaaa     60

gcaagggcca gccatacgga cggcgctact cgcgtacaac gtctctggcg tccgtaggtg    120

aacctgcgga aggatcatta ccgagtgcgg gtctttatgg cccaacctcc cacccgtgac    180

tattgtacct tgttgcttcg gcgggcccgc cagcgttgct ggccgccggg gggcgactcg    240

cccccgggcc cgtgcccgcc ggagacccca acatgaaccc tgttctgaaa gcttgcagtc    300

tgagtgtgat tctttgcaat cagttaaaac tttcaacaat ggatctcttg gttccggcat    360

cgatgaagaa cgcagcgaaa tgcgataact aatgtgaatt gcagaattca gtgaatcatc    420

gagtctttga acgcacattg cgccccctgg tattccgggg ggcatgcctg tccgagcgtc    480

attgctgccc tcaagcccgg cttgtgtgtt gggccctcgt cccccggctc ccgggggacg    540

ggcccgaaag gcagcggcgg caccgcgtcc ggtcctcgag cgtatggggc ttcgtcttcc    600

gctccgtagg cccggccggc gcccgccgac gcatttattt gcaacttgtt tttttccagg    660

ttgacctcgg atcaggtagg gatac                                          685
```

<210> SEQ ID NO 5
<211> LENGTH: 676
<212> TYPE: DNA
<213> ORGANISM: Aspergillus niger

<400> SEQUENCE: 5

```
ggaagtaaaa gtcgtaacaa ggtttctgta ggtgaacctg cagaaggatc attagtgaaa     60

gcaagggcca gccatacgga cggcgctact cgcgtacaac gtctctggcg tccgtaggtg    120

aacctgcgga aggatcatta ccgagtgcgg gtcctttggg cccaacctcc catccgtgtc    180

tattgtaccc tgttgcttcg gcgggcccgc cgcttgtcgg ccgccggggg ggcgcctctg    240

ccccccgggc ccgtgcccgc cggagacccc aacacgaaca ctgtctgaaa gcgtgcagtc    300

tgagttgatt gaatgcaatc agttaaaact ttcaacaatg gatctcttgg ttccggcatc    360

gatgaagaac gcagcgaaat gcgataacta atgtgaattg cagaattcag tgaatcatcg    420

agtctttgaa cgcacattgc gccccctggt attccggggg gcatgcctgt ccgagcgtca    480

ttgctgccct caagcccggc ttgtgtgttg ggtcgccgtc cccctctccg gggggacggg    540

cccgaaaggc agcggcggca ccgcgtccga tcctcgagcg tatggggctt tgtcacatgc    600

tctgtaggat tggccggcgc ctgccgacgt tttccaacca ttctttccag gttgacctcg    660

gatcaggtag ggatac                                                    676
```

<210> SEQ ID NO 6
<211> LENGTH: 642
<212> TYPE: DNA
<213> ORGANISM: Aspergillus nidulans

<400> SEQUENCE: 6

```
ggaagtaaaa gtcgtaacaa ggtttctgta ggtgaacctg cagaaggatc attagtgaaa     60
```

-continued

```
gcaagggcca gccatacgga cggcgctact cgcgtacaac gtctctggcg tccgtaggtg    120

aacctgcgga aggatcatta ccgagtgcgg gctgcctccg ggcgcccaac ctcccacccg    180

tgactactaa cactgttgct tcggcgggga gccccccagg ggcgagccgc cggggaccac    240

tgaacttcat gcctgagagt gatgcagtct gagcctgaat acaaatcagt caaaactttc    300

aacaatggat ctcttggttc cggcatcgat gaagaacgca gcgaactgcg ataagtaatg    360

tgaattgcag aattcagtga atcatcgagt ctttgaacgc acattgcgcc ccctggcatt    420

ccgggggca tgcctgtccg agcgtcattg ctgccctcaa gcccggcttg tgtgttgggt     480

cgtcgtcccc cccgggggac gggcccgaaa ggcagcggcg gcaccgtgtc cggtcctcga    540

gcgtatgggg ctttgtcacc cgctcgatta gggccggccg ggcgccagcc ggcgtctcca    600

accttatttt tctcaggttg acctcggatc aggtagggat ac                        642
```

<210> SEQ ID NO 7
<211> LENGTH: 674
<212> TYPE: DNA
<213> ORGANISM: Aspergillus fumigatus

<400> SEQUENCE: 7

```
ggaagtaaaa gtcgtaacaa ggtttctgta ggtgaacctg cagaaggatc attagtgaaa     60

gcaagggcca gccatacgga cggcgctact cgcgtacaac gtctctggcg tccgtaggtg    120

aacctgcgga aggatcatta ccgagtgagg gccctttggg tccaacctcc cacccgtgtc    180

tatcgtacct tgttgcttcg gcgggcccgc cgtttcgacg gccgccgggg aggccttgcg    240

cccccgggcc cgcgcccgcc gaagacccca acatgaacgc tgttctgaaa gtatgcagtc    300

tgagttgatt atcgtaatca gttaaaactt tcaacaacgg atctcttggt tccggcatcg    360

atgaagaacg cagcgaaatg cgataactaa tgtgaattgc agaattcagt gaatcatcga    420

gtctttgaac gcacattgcg ccccctggta ttccgggggg catgcctgtc cgagcgtcat    480

tgctgccctc aagcacggct tgtgtgttgg gcccccgtcc ccctctcccg gggggacgggc    540

ccgaaaggca gcggcggcac cgcgtccggt cctcgagcgt atggggcttt gtcacctgct    600

ctgtaggccc ggccggcgcc agccgacacc caactttatt tttctaaggt tgacctcgga    660

tcaggtaggg atac                                                       674
```

<210> SEQ ID NO 8
<211> LENGTH: 672
<212> TYPE: DNA
<213> ORGANISM: Aspergillus flavus

<400> SEQUENCE: 8

```
ggaagtaaaa gtcgtaacaa ggtttctgta ggtgaacctg cagaaggatc attagtgaaa     60

gcaagggcca gccatacgga cggcgctact cgcgtacaac gtctctggcg tccgtaggtg    120

aacctgcgga aggatcatta ccgagtgtag ggttcctagc gagcccaacc tcccacccgt    180

gtttactgta ccttagttgc ttcggcgggc ccgccattca tggccgccgg gggctctcag    240

ccccgggccc gcgcccgccg gagacaccac gaactctgtc tgatctagtg aagtctgagt    300

tgattgtatc gcaatcagtt aaaactttca acaatggatc tcttggttcc ggcatcgatg    360

aagaacgcag cgaaatgcga taactagtgt gaattgcaga attccgtgaa tcatcgagtc    420

tttgaacgca cattgcgccc cctggtattc cggggggcat gcctgtccga gcgtcattgc    480

tgcccatcaa gcacggcttg tgtgttgggt cgtcgtcccc tctccggggg ggacgggccc    540
```

-continued caaaggcagc ggcggcaccg cgtccgatcc tcgagcgtat ggggctttgt cacccgctct 600
gtaggcccgg ccggcgcttg ccgaacgcaa atcaatcttt ttccaggttg acctcggatc 660
aggtagggat ac 672

<210> SEQ ID NO 9
<211> LENGTH: 799
<212> TYPE: DNA
<213> ORGANISM: Pseudallescheria boydii

<400> SEQUENCE: 9
ggaagtaaaa gtcgtaacaa ggtttctgta ggtgaacctg cagaaggatc attagtgaaa 60
gcaagggcca gccatacgga cggcgctact cgcgtacaac gtctctggcg tccgtaggtg 120
aacctgcgga gggatcatta cagagttact actccaaacc cattgtggga agtaaaagtc 180
gtaacaaggt ttctgtaggt gaacctgcag aaggatcatt agtgaaagca agggccagcc 240
atacggacgg cgctactcgc gtacaacgtc tctggcgaac cttacctatg ttctgttgcc 300
tcggcggcgt ggtcagcgcc ccctctgaaa agaggacgat gtcctcccgc cggcagcacc 360
aaactctttg aattttacag cggatcacag ttctgatttg aaaacaaaaa acaagttaaa 420
actttcaaca acggatctct tggttctggc atcgatgaag aacgcagcga aatgcgataa 480
gtaatgtgaa ttgcagaatt cagtgaatca tcgaatcttt gaacgcacat tgcgcccggc 540
agtaatctgc cgggcatgcc tgtccgagcg tcatttcaac cctcgaacct ccgtttcctc 600
agggaagctc agggtcggtg ttggggcgct acggcgagtc ttcgcgaccc tccgtaggcc 660
ctgaaataca gtggcggtcc cgccgcggtt gccttctgcg tagtaagtct cttttgcaag 720
ctcgcattgg gtcccggcgg aggcctgccg tcaaaccacc tataactcca gatggttgac 780
ctcggatcag gtagggtac 799

<210> SEQ ID NO 10
<211> LENGTH: 563
<212> TYPE: DNA
<213> ORGANISM: Fusarium solani
<220> FEATURE:
<221> NAME/KEY: misc_feature
<222> LOCATION: (0)...(0)
<223> OTHER INFORMATION: n = a or c or g or t

<400> SEQUENCE: 10
ggaagtaaaa gtcgtaacaa ggtttctgta ggtgaacctg cagaaggatc attcgagtta 60
tacaactcat caaccctgtg aacataccta taacgttgcc tcggcgggaa cagacggccc 120
cgtaacacgg gccgcccccg ccagaggacc ccctaactct gtttctataa tgtttcttct 180
gagtaaacaa gcaaataaat taaaactttc aacaacggat ctcttggctc tggcatcgat 240
gaagaacgca gcgaaatgcg ataagtaatg tgaattgcag aattcagtga atcatcgaat 300
ctttgaacgc acattgcgcc cgccagtatt ctggcgggca tgcctgttcg agcgtcatta 360
caaccctcag ggccccgggc ctggcgttgg ggatcggcgg aagcccccctg cgggcacaac 420 gccgtccccc aaatacagtg gcggggcccg ccgcaaactt ccattgcggt anatatacta 480
acacctcgca aatggagaga gggggcggcc acgccgtaaa acacccaact tctgaatgtt 540
gacctcgaat caagtaggaa tac 563

<210> SEQ ID NO 11
<211> LENGTH: 620
<212> TYPE: DNA
<213> ORGANISM: Fusarium oxysporum -continued

<400> SEQUENCE: 11

```
ggaagtaaaa gtcgtaacaa ggtttctgta ggtgaacctg cagaaggatc attagtgaaa     60
gcaagggcca gccatacgga cggcgctact cgcgtacaac gtctctggcg tccgtaggtg    120
aacctgcggt gggtcattac cgagtttaca actcccaaac ccctgtgaac ataccacttg    180
ttgcctcggc ggatcagccc gctcccggta aaacgggacg gcccgccaga ggacccctaa    240
actctgtttc tatatgtaac ttctgagtaa aaccataaat aaatcaaaac tttcaacaac    300
ggatctcttg gttctggcat cgatgaagaa cgcagcaaaa tgcgataagt aatgtgaatt    360
gcagaattca gtgaatcatc gaatctttga acgcacattg cgcctgccag tattctggcg    420
ggcatgcctg ttcgagcgtc atttcaaccc tcaagcacag cttggtgttg ggactcgcgt    480
taattcgcgt tccccaaatt gattggcggt cacgtcgagc ttccatagcg tagtagtaaa    540
accctcgtta ctggtaatcg tcgcggccac gccgttaaac ccccaacttct gaatgttgac    600
ctcggatcag gtaggaatac                                                620
```

<210> SEQ ID NO 12
<211> LENGTH: 637
<212> TYPE: DNA
<213> ORGANISM: Fusarium monilliformes

<400> SEQUENCE: 12

```
ggaagtaaaa gtcgtaacaa ggtttctgta ggtgaacctg cagaaggatc attagtgaaa     60
gcaagggcca gccatacgga cggcgctact cgcgtacaac gtctctggcg tccgtaggtg    120
aacctgcgga gggatcatta cagagttact acaactccca aacccctgtg aacatacgaa    180
ttgttgcctc ggcggatcag cccgctcccg gtaaaacggg acggcccgcc agaggacccc    240
taaactctgt ttctatatgt aacttctgag taaaaccata aataaatcaa aactttcaac    300
aacggatctc ttggttctgg catcgatgaa gaacgcagca aaatgcgata agtaatgtga    360
attgcagaat tcagtgaatc atcgaatctt tgaacgcaca ttgcgcccgc cagtattctg    420
gcgggcatgc ctgttcgagc gtcatttcaa ccctcaagcc cccgggtttg gtgttgggga    480
tcggcgagcc cttgcggcaa gccggccccg aaatctagtg gcggtctcgc tgcagcttcc    540
attgcgtagt agtaaaaccc tcgcaactgg tacgcggcgc ggccaagccg ttaaaccccc    600
aacttctgaa tgttgacctc ggatcaggta ggaatac                             637
```

<210> SEQ ID NO 13
<211> LENGTH: 631
<212> TYPE: DNA
<213> ORGANISM: Malassezia furfur

<400> SEQUENCE: 13

```
ggaagtaaaa gtcgtaacaa ggtttctgta ggtgaacctg cagaaggatc attagtgaaa     60
gcaagggcca gccatacgga cggcgctact cgcgtacaac gtctctggcg cccaacttta    120
cacaatatcc acaaacccgt gtgcaccgtt tggatgagtt ggacctcgca agaggctcgg    180
ctctccaatc catttctacc aaactcgtat ggtttgtatg aacgtggaaa tcgttggacc    240
gtaactggcc aacaaccaat aatacaactt tcgacaacgg atctcttggt tctcccatcg    300
atgaagaacg cagcgaaacg cgataggtaa tgtgaattgc agaattccgt gaatcatcga    360
atctttgaac gcaccttgcg ctccatggta ttccgtggag catgcctgtt tgagtgccgt    420
gaattctctc tccccaagcg gttgcgattg cactgctttg gcggacgagg ttggatgggt    480
```

-continued

```
gcttctgcct gtttcgcaag aaacaggctc gcccgaaatg cattagcgcc tttgggacac    540

actctgcaaa ccgctcttga aaggggaagg ccggcagaag gggatggagg aactccgccc    600

gtcagctata cctcggatca ggtagggata c                                   631
```

<210> SEQ ID NO 14
<211> LENGTH: 648
<212> TYPE: DNA
<213> ORGANISM: Cylindrocarpon lichenicola

<400> SEQUENCE: 14

```
ggaagtaaaa gtcgtaacaa ggtttctgta ggtgaacctg cagaaggatc attagtgaaa     60

gcaagggcca gccatacgga cggcgctact cgcgtacaac gtctctggcg tccgtaggtg    120

aacctgcgga aggatcatta cacaaatatg aaggcgggct ggaacctctc ggggttacag    180

ccttgctgaa ttattcaccc ttgtcttttg cgtacttctt gtttccttgg tgggttcgcc    240

caccactagg acaaacataa acctttttgta attgcaatca gcgtcagtaa caaattaata    300

attacaactt tcaacaacgg atctcttggt tccggcatcg atgaagaacg cagcgaaatg    360

cgataagtaa tgtgaattgc agaattccgt gaatcatcga atctttgaac gcacattgcg    420

ccctttggta ttccgggggg catgcctgtc cgagcgtcat ttgtaccctc aagctttgct    480

tggtgttggg cgtcttgtct ctagctttgc tggagactcg ccttaaagta attggcagcc    540

ggcctactgg tttcggagcg cagcacaagt cgcactctct atcagcaaag gtctagcatc    600

cattaagcct ttttttcaac ttttgacctc ggatcaggta gggatacc                 648
```

<210> SEQ ID NO 15
<211> LENGTH: 734
<212> TYPE: DNA
<213> ORGANISM: Cladophialophora bantiana

<400> SEQUENCE: 15

```
ggaagtaaaa gtcgtaacaa ggtttccgta ggtgaacctg cggaaggatc attaacgagt     60

tagggtctcc caggcccggc cggaagtaaa agtcgtaaca aggtttctgt aggtgaacct    120

gcagaaggat cattagtgaa agcaagggcc agccatacgg acggcgctac tcgcgtacaa    180

cgtctctggc gtcccaaccc tttgtttatt aaacctctgt tgcttcggcg gacccgtctt    240

ccctgaccgc cggaggaccg ccgactcggc gtcctctggc cagcgtccgc cgggggcctc    300

ttctccaaac tctggttaag catgattttg tgtctgagtg atttgtatca aatcaaaagc    360

aaaaactttc aacaacggat ctcttggttc tggcatcgat gaagaacgca gcgaaatgcg    420

ataagtaatg cgaattgcag aattccagtg agtcatcgaa tctttgaacg cacattgcgc    480

cctttggtat tccgaagggc atgcctgttc gagcgtcatt atcaccccctc aagccctcgt    540

gcttggtgtt ggacggtctg gcggaagtgt cgtgcacccc gcccctccta aagacaatga    600

cggcggcctc gtggaacccc cggtacactg agcttcttta ccgagcacgt atcggatcaa    660

gggcgcccgg gacacggtct tctccctcat gtgggaaaca ttgcaaggtt gacctcggat    720

caggtaggaa tacg                                                      734
```

<210> SEQ ID NO 16
<211> LENGTH: 700
<212> TYPE: DNA
<213> ORGANISM: Gymnascella hyalinaspora

<400> SEQUENCE: 16

```
ggaagtaaaa gtcgtaacaa ggtttctgta ggtgaacctg cagaaggatc attagtgaaa     60
```

gcaagggcca gccatacgga cggcgctact cgcgtacaac gtctctggcg tccgtaggtg 120
aacctgcgga aggatcatta cagtgccgcc gggacgcgcc ccctaaaccg gggcgtgctc 180
ccgcaactgg ccacccgtgt ctaccgaacc tcgttgcttt ggcgggcccg cgaacccctc 240
acggggggag ccgccttggg gagcagtccc cgggcccgcg cccgccagag aaccacaact 300
gaactctttg ctgatgagtg actgtctgag tgattgattt aatcattaaa actttcaaca 360
acggatctct tggttccagc atcgatgaag aacgcagcga aatgcgataa gtaatgtgaa 420
ttgcagaatt ccgtgaatca tcgaatcttt gaacgcacat tgcgccctct ggtattccgg 480
ggggcatgcc tgtccgagcg tcattgcacc aatcaagccc ggcttgtgtg atgggtcttc 540
attcgtcccg aatgggggac gggcccgaaa tgcagtggcg gcgtcgtggt tatccaacgg 600
cctgagtgta tggggctctg tcacacgctc accagccagg accggcgcca gcctaccagt 660
ctattcttct taggttgacc tcggatcagg tagggatacc 700

<210> SEQ ID NO 17
<211> LENGTH: 692
<212> TYPE: DNA
<213> ORGANISM: Blastomyces dermatitides
<220> FEATURE:
<221> NAME/KEY: misc_feature
<222> LOCATION: (0)...(0)
<223> OTHER INFORMATION: n = a or c or g or t

<400> SEQUENCE: 17
ggaagtaaaa gtcgtaacaa ggtttctgta ggtgaacctg cagaaggatc attagtgaaa 60
gcaagggcca gccatacgga cggcgctact cgcgtacaac gtctctggcg ttaacgcgcc 120 gngggggtt ggacctccta gaccggagga accccggccc cctcacctgg ccacccttgt 180
ctatttttac ctgttgcttc ggcgggcctg cagcgatgct gccgggggag ttttcactcc 240
ccgggctcgt gcccgccgag gacaccgcta gaacttctgg tgaacgattg acatctgaga 300
aaataactat aatcagttaa aactttcaac aacggatctc ttggttccga catcgatgaa 360
gaacgcagcg aaatgcgata agtaatgtga attgcagaat tccgtgaatc atcgaatctt 420
tgaacgcaca ttgcgccctc tggtattccg gggggcatgc ctgtccgagc gtcattgcaa 480
ccctcaagcg cggcttgtgt gttgggcctt cgtccccccg tggacgtgcc cgaaatgcag 540
cggcggcgtc gtgttccggt gcccgagcgt atggggcttt gtcacccgct ctagaggccc 600
ggccggctcc ggccccatct caaacccttc gagggagggc ggtcttcggg ccggtctccc 660
caccaggttg acctcggatc aggtaggaat ac 692

<210> SEQ ID NO 18
<211> LENGTH: 618
<212> TYPE: DNA
<213> ORGANISM: Histoplasma duboisii

<400> SEQUENCE: 18
ggaagtaaaa gtcgtaacaa ggtttctgta ggtgaacctg cagaaggatc attagtgaaa 60
gcaagggcca gccatacgga cggcgctact cgcgtacaac gtctctggcg tccgtaggtc 120
gccgtggggg gttgggagtc tctgaccggg accccctccgc cccccttacc cggccatcct 180
tgtctaccgg acctgttgcc tcggcgggcc tgcagcgatg ctgccggggg agcttcttct 240
ccccgggctc gtgtccgccg gggacaccgc aagaaccgtc ggtgaacgat tggcgtctga 300
gcataagagc gataataatc cagttaaaac tttcaacaac ggatctcttg gttccgacat 360

-continued

```
cgatgaagaa cgcagcgaaa tgcgataagt aatgtgaatt gcagaattcc gtgaatcatc    420

gaatctttga acgcacattg cgccccctgg tattccgggg ggcatgcctg tccgagcgtc    480

attgcaaccc tcaagcgcgg cttgtgtttt gggccgtcgt ccccccctcga ccggcgggac    540

ttgccccgaa atgcagttgg cggtgtcgag ttccggttgc cccgagcgtt atggctttgc    600

cacccgctct ggaagccc                                                  618
```

```
<210> SEQ ID NO 19
<211> LENGTH: 618
<212> TYPE: DNA
<213> ORGANISM: Histoplasma capsulatum

<400> SEQUENCE: 19

ggaagtaaaa gtcgtaacaa ggtttctgta ggtgaacctg cagaaggatc attagtgaaa     60

gcaagggcca gccatacgga cggcgctact cgcgtacaac gtctctggcg tccgtaggtc    120

gccgtggggg gttgggagtc tctgaccggg acccctccgc ccccttacc cggccatcct    180

tgtctaccgg acctgttgcc tcggcgggcc tgcagcgatg ctgccggggg agcttcttct    240

ccccgggctc gtgtccgccg gggacaccgc aagaaccgtc ggtgaacgat tggcgtctga    300

gcataagagc gataataatc cagttaaaac tttcaacaac ggatctcttg gttccgacat    360

cgatgaagaa cgcagcgaaa tgcgataagt aatgtgaatt gcagaattcc gtgaatcatc    420

gaatctttga acgcacattg cgccccctgg tattccgggg ggcatgcctg tccgagcgtc    480

attgcaaccc tcaagcgcgg cttgtgtttt gggccgtcgt ccccccctcga ccggcgggac    540

ttgccccgaa atgcagttgg cggtgtcgag ttccggttgc cccgagcgtt atggctttgc    600

cacccgctct ggaagccc                                                  618
```

```
<210> SEQ ID NO 20
<211> LENGTH: 577
<212> TYPE: DNA
<213> ORGANISM: Cryptococcus neoformans

<400> SEQUENCE: 20

ggaagtaaaa gtcgtaacaa ggtttctgta ggtgaacctg cagaaggatc attagtgaaa     60

gcaagggcca gccatacgga cggcgctact cgcgtacaac gtctctggcg gagaatattg    120

gactttggtc catttatcta cccatctaca cctgtgaact gtttatgtgc ttcggcacgt    180

tttacacaaa cttctaaatg taatgaatgt aatcatatta taacaataat aaaactttca    240

acaacggatc tcttggcttc cacatcgatg aagaacgcag cgaaatgcga taagtaatgt    300

gaattgcaga attcagtgaa tcatcgagtc tttgaacgca acttgcgccc tttggtattc    360

cgaagggcat gcctgtttga gagtcatgaa aatctcaatc cctcgggttt tattacctgt    420

tggacttgga tttgggtgtt tgccgcgacc tgcaaaggac gtcggctcgc cttaaatgtg    480

ttagtgggaa ggtgattacc tgtcagcccg gcgtaataag tttcgctggg cctatggggt    540

agtcttcggc ttgctgataa caaccatctc tttttgt                              577
```

```
<210> SEQ ID NO 21
<211> LENGTH: 498
<212> TYPE: DNA
<213> ORGANISM: Issatchenkia orientalis

<400> SEQUENCE: 21

ggaagtaaaa gtcgtaacaa ggtttccgta ggtgaacctg cggaaggatc attactgtga     60

tttagtacta cactgcgtga gcggaacgaa aacaacaaca cctaaaatgt ggaatatagc    120
```

-continued

```
atatagtcga caagagaaat ctacgaaaaa caaacaaaac tttcaacaac ggatctcttg    180

gttctcgcat cgatgaagag cgcagcgaaa tgcgatacct agtgtgaatt gcagccatcg    240

tgaatcatcg agttcttgaa cgcacattgc gcccctcggc attccggggg gcatgcctgt    300

ttgagcgtcg tttccatctt gcgcgtgcgc agagttgggg gagcggagcg gacgacgtgt    360

aaagagcgtc ggagctgcga ctcgcctgaa agggagcgaa gctggccgag cgaactagac    420

ttttttcag ggacgcttgg cggccgagag cgagtgttgc gagacaacaa aaagctcgac    480

ctcagatcag gtaggaat                                                  498
```

<210> SEQ ID NO 22
<211> LENGTH: 646
<212> TYPE: DNA
<213> ORGANISM: Candida albicans

<400> SEQUENCE: 22

```
ggaagtaaaa gtcgtaacaa ggtttctgta ggtgaacctg cagaaggatc attagtgaaa     60

gcaagggcca gccatacgga cggcgctact cgcgtacaac gtctctggcg tccgtaggtg    120

aacctgcgga aggatcatta ctgatttgct taattgcacc acatgtgttt ttctttgaaa    180

caaacttgct ttggcggtgg gcccagcctg ccgccagagg tctaaactta caaccaattt    240

tttatcaact tgtcacacca gattattact aatagtcaaa actttcaaca acggatctct    300

tggttctcgc atcgatgaag aacgcagcga aatgcgatac gtaatatgaa ttgcagatat    360

tcgtgaatca tcgaatcttt gaacgcacat tgcgccctct ggtattccgg agggcatgcc    420

tgtttgagcg tcgtttctcc ctcaaaccgc tgggtttggt gttgagcaat acgacttggg    480

tttgcttgaa agacggtagt ggtaaggcgg gatcgctttg acaatggctt aggtctaacc    540

aaaaacattg cttgcggcgg taacgtccac cacgtatatc ttcaaacttt gacctcaaat    600

caggtaggac tacccgctga acttaagcat atcaataagc ggagga                   646
```

<210> SEQ ID NO 23
<211> LENGTH: 323
<212> TYPE: DNA
<213> ORGANISM: Candida Lusitaniae

<400> SEQUENCE: 23

```
aaaaatacat tacacattgt ttttgcgaac aaaaaaataa attttttat tcgaatttct      60

taatatcaaa actttcaaca acggatctct tggttctcgc atcgatgaag aacgcagcga    120

attgcgatac gtagtatgac ttgcagacgt gaatcatcga atctttgaac gcacattgcg    180

cctcgaggca ttcctcgagg catgcctgtt tgagcgtcgc atcccctcta acccccggtt    240

aggcgttgct ccgaaatatc aaccgcgctg tcaaacacgt ttacagcacg acatttcgcc    300

ctcaaatcag gtaggactac ccg                                            323
```

<210> SEQ ID NO 24
<211> LENGTH: 559
<212> TYPE: DNA
<213> ORGANISM: Candida glabrata

<400> SEQUENCE: 24

```
aagaatttaa ttgatttgtc tgagctcgga gagagacatc tctggggagg accagtgtga     60

cactcaggag gctcctaaaa tattttctct tctgtgaatg ctatttctcc tgcctgcgct    120

taagtgcgcg gttggtgggt gttctgcagt gggggaggg agccgacaaa gacctgggag    180
```

```
tgtgcgtgga tctctctatt ccaaaggagg tgttttatca cacgactcga cactttctaa    240

ttactacaca cagtggagtt tactttacta ctattctttt gttcgttggg ggaacgctct    300

ctttcggggg ggagttctcc caatggatgc caacacaaac aaatattttt ttaaacttat    360

tcaatcaaca caagatttct tttaatagaa aacaacttca aaactttcaa caatggatct    420

cttggttctc gcatcgatga agaacgcagc gaaatgccga tacgtaatgt gaattgcaga    480

attccgtgaa tcatcgaatc tttgaacgca cattgcgccc tctggtattc cgggggggcat    540

gcctgtttga gcgtcattt                                                 559
```

```
<210> SEQ ID NO 25
<211> LENGTH: 520
<212> TYPE: DNA
<213> ORGANISM: Penicillium spp.
<220> FEATURE:
<221> NAME/KEY: misc_feature
<222> LOCATION: (0)...(0)
<223> OTHER INFORMATION: n = a or c or g or t

<400> SEQUENCE: 25

ggaagtaaaa gtcgtaacaa ggtttctgta ttgttgcttc ggcgggcccg ccttaactgg     60

ccgccggggg gcttacgccc ccgggcccgc gcccgccgaa gacaccctcg aactctgtct    120

gaagattgta gtctgagtga aaatataaat tatttaaaac tttcaacaac ggatctcttg    180

gttccggcat cgatgaagaa cgcagcgaaa tgcgatacgt aatgtgaatt gcaaattcag    240

tgaatcatcg agtctttgaa cgcacattgc gccccctggt attccggggg gcatgcctgt    300

ccgagcgtca ttgctgccct caagcacggc ttgtgtgttg ggcccccgtc ctcccgatcc    360

cgggggacgg cccccgaaaa ggcagcggcg gcaccgcctt cccggtcctc cgagccttat    420

ggggctttgt tcaccccgct cttgttaggc cccggcccgc ctgcccccga tcaacccaaa    480

tttttatcca agtttgacct ccggatcang ttagggatac                         520
```

```
<210> SEQ ID NO 26
<211> LENGTH: 654
<212> TYPE: DNA
<213> ORGANISM: Malbranchia spp.

<400> SEQUENCE: 26

ggaagtaaaa gtcgtaacaa ggtttctgta ggtgaacctg cagaaggatc attagtgaaa     60

gcaagggcca gccatacgga cggcgctact cgcgtacaac gtctctggcg tccgtaggtg    120

aacctgcgga aggatcatta aagtgttaag ccggcgcctc cgtgtgccgg tgaaactcca    180

cccttgacta ctataccaca tgttgctttg gcgggcccgc ctccgggccg ccgggggccc    240

tgcccctggc ccgcgcccgc cagagataca ctgaaccctt tgtgaaattg gacgtctgag    300

ttgatgatca atcattaaaa ctttcaacaa tggatctctt ggttccggca tcgatgaaga    360

acgcagcgaa atgcgataag taatgtgaat tgcagaattc cgtgaatcat cgaatctttg    420

aacgcacatt gcgccccctg gtattccggg gggcatgcct gtccgagcgt cattgcaacc    480

ctcaagcgcg gcttgtgtgt tgggcctcgt cccccgtgga cgtgcccgaa aggcagtggc    540

ggcgtccgtt tcggtgcccg agcgtatggg aactcttata ccgctcgaag ggcccggcgg    600

cgctggtcag aaccaaatct tttaccggtt gacctcggat caggtaggga tacc          654
```

```
<210> SEQ ID NO 27
<211> LENGTH: 719
<212> TYPE: DNA
<213> ORGANISM: Arthrogrothilus spp.
```

<220> FEATURE:
<221> NAME/KEY: misc_feature
<222> LOCATION: (0)...(0)
<223> OTHER INFORMATION: n = a or c or g or t

<400> SEQUENCE: 27

```
ggaagtaaaa gtcgtaacaa ggtttctgta ggtgaacctg cagaaggatc attagtgaaa     60

gcaagggcca gccatacgga cggcgctact cgcgtacaac gtctctggcg tatggtgtct    120

tggttgtagc tggctcctcg gagcattgtg cacgcccgcc atttttatct atccacctgt    180

gcaccgactg taggtctgga tgactctcgt gctctctgag tgcggatgcg aggattgccc    240

tcttgaggtg tctctcctcg aatttccagg ctctacgtct ttttacacac cccacaagta    300

tgatatagaa tgtagtcaat gggcttgatc gcctataaaa cactatacaa ctttcagcaa    360

cggatctctt ggctctcgca tcgatgaaga acgcagcgaa atgcgataag taatgtgaat    420

tgcagaattc agtgaatcat cgaatctttg aacgcacctt gcgctccttg gtattccgag    480

gagcatgcct gtttgagttg tcattaaatt ctcaacctca ccccgttttc ccgaacggtt    540

ctccgaggct tggatgtggg tttttgtgcc aggcttgcct ccagccgcgg tcttgtcccc    600

ttgaaattgc atttagcgag ttcgtacttg agctccgtct atggtngtga taaattatct    660

acgcccgttg gacngtttta aaactccctt ctaaccgtcc cgcaangana atanctttt     719
```

<210> SEQ ID NO 28
<211> LENGTH: 672
<212> TYPE: DNA
<213> ORGANISM: Cylindrocarpon destructans

<400> SEQUENCE: 28

```
ggaagtaaaa gtcgtaacaa ggtttctgta ggtgaacctg cagaaggatc attagtgaaa     60

gcaagggcca gccatacgga cggcgctact cgcgtacaac gtctctggcg tccgtaggtg    120

aacctgcgga aggatcatta cagtgccgcc gggacgcgcc ccctaaaccg gggcgccgag    180

tttacaactc ccaaacccct gtgaacatac catttgttgc ctcggcggtg cctgcttcgg    240

cagcccgcca gaggacccaa acccttgatt ttatacagta tcttctgagt aaatgattaa    300

ataaatcaaa actttcaaca acggatctct tggttctggc atcgatgaag aacgcagcga    360

aatgcgataa gtaatgtgaa ttgcagaatt cagtgaatca tcgaatcttt gaacgcacat    420

tgcgcccgcc agtattctgg cgggcatgcc tgttcgagcg tcatttcaac cctcaagccc    480

ccgggcttgg tgttggagat cggcgtgccc cccggggcgc gccggctccc aaatatagtg    540

gcggtctcgc tgtagcttcc tctgcgtagt agcacacctc gcactggaaa acagcgtggc    600

cacgccgtta aaccccccac ttctgaaagg ttctattctt cttaggttga cctcggatca    660

ggtagggata cc                                                        672
```

<210> SEQ ID NO 29
<211> LENGTH: 727
<212> TYPE: DNA
<213> ORGANISM: Sporothrix schenkii
<220> FEATURE:
<221> NAME/KEY: misc_feature
<222> LOCATION: (0)...(0)
<223> OTHER INFORMATION: n = a or c or g or t

<400> SEQUENCE: 29

```
ggaagtaaaa gtcgtaacaa ggtttctgta ggtgaacctg cagaaggatc attagtgaaa     60

gcaagggcca gccatacgga cggcgctact cgcgtacaac gtctctggcg gtcgtaacaa    120
```

```
ggtctccgtt ggtgaaccag cggagggatc attacagagt tttcacaact cccaaccctt    180

gcgaaccgta cccaatctcg ttctcgttgc ttctggcggg gggaancggg ggggcgcccn    240

acacggcccc ctcttgcccc cgcccgccag gggcggcggg ccctacgaac ctttgtatct    300

caaccactag aaaaccgtct gaggaaaaaa caaaataatc aaaactttca acaacggatc    360

tcttggctct ggcatcgatg aagaacgcag cgaaatgcga tacgtaatgt gaattgcaga    420

attcagcgaa ccatcgaatc tttgaacgca cattgcgccc gccagcattc tggcgggcat    480

gcctgtccga gcgtcatttc ccccctcacg cgccccgttg cgcgctggtg ttggggcgcc    540

ctccgcctgg cggggggccc ccgaaancga gtggcgggcc ctgtggaagg ctccgagcgc    600

agtaccgaac gcatgttctc cctcgctcc ggacgccccc caggcgccct gccgtgaaaa    660

cgcgcatgac gcgcagctct ttttacaagg ttgacctcgc cgctgacctc ggatcagtag    720

ggaatac                                                              727
```

<210> SEQ ID NO 30
<211> LENGTH: 700
<212> TYPE: DNA
<213> ORGANISM: Penicillium marnefeii

<400> SEQUENCE: 30

```
ggaagtaaaa gtcgtaacaa ggtttctgta ggtgaacctg cagaaggatc attagtgaaa     60

gcaagggcca gccatacgga cggcgctact cgcgtacaac gtctctggcg tccgtaggtg    120

aacctgcgga aggatcatta ccgagtgagg gccctctggg tccaacctcc cacccgtgtc    180

tatcgtacct tgttgcttcg gcgggcccgc cgtttcgacg gccaccgggg aggccttgcg    240

cccccgggcc cgcgcccgcc gaagacccca acatgaacgc tgttctgaaa gtatgcagtc    300

tgagttgatt atcgtaatca gttaaaactt tcaacaacgg atctcttggt tccggcatcg    360

atgaagaacg cagcgaaatg cgataagtaa tgtgaattgc agaattcagt gaatcatcga    420

gtctttgaac gcacattgcg ccccctggta ttccgggggg catgcctgtc cgagcgtcat    480

tgctgccctc aagcacggct tgtgtgtggg cccccgtccc cctctcccgg gggacgggcc    540

cgaaaggcag cggcggcacc gcgtccggtc ctcgagcgta tggggctttg tcacctgctc    600

tgtaggcccg gccggcgcca gccgacaccc aactttattt ttctaaggtt gaccttggat    660

caggtaggga tacccgctgc ctcggatcag gtaggaatac                          700
```

<210> SEQ ID NO 31
<211> LENGTH: 714
<212> TYPE: DNA
<213> ORGANISM: Coccidiodes immitis

<400> SEQUENCE: 31

```
ggaagtaaaa gtcgtaacaa ggtttctgta ggtgaacctg cagaaggatc attagtgaaa     60

gcaagggcca gccatacgga cggcgctact cgcgtacaac gtctctggcg tccgtaggtg    120

cgtccggctg cgcacctccc ccgcgggggt tcgcgcggtc cgtacctccc acccgtgttt    180

actgaaccat tgttgccttg gcaggcctgc cgggcctccg gctgccgggg atcgcccgcc    240

ttgcgcggcg tcccgggcgc gcgcctgcca gcggatcaat tgaactctta tgtgaagatt    300

gtcagtctga gcatcatagc aaaaatcaaa caaaactttc aacaacggat ctcttggttc    360

cggcatcgat gaagaacgca gcgaaatgcg ataagtaatg tgaattgcag aattccgtga    420

atcatcgaat ctttgaacgc acattgcgcc ctctggtatt ccggggggca tgcctgttcg    480

agcgtcattg caaacccttc aagcacggct tgtgtgttgg gccaacgtcc ccgcttgtgt    540
```

-continued

```
ggacgggcct gaaatgcagt ggcggcaccg agttcctggt gtctgagtgt atgggaaatc    600

acttcatcgc tcaaagaccc gatcggggcc gatctctttt ttttattata tccggtttga    660

cctcggatca ggtaggagta cccgctgaac ttacctcgga tcaggtagga atac          714


<210> SEQ ID NO 32
<211> LENGTH: 497
<212> TYPE: DNA
<213> ORGANISM: Candida tropicalis
<220> FEATURE:
<221> NAME/KEY: misc_feature
<222> LOCATION: (0)...(0)
<223> OTHER INFORMATION: n = a or c or g or t

<400> SEQUENCE: 32

ggaagtaaaa agtcgtaaca aggtttccga ggngaacctg cggaaggatc nttactgatt     60

tgcttaantg ccccncatgn gttttttatt naacaaattt ntttggnggc gggancaatc    120

cnaccnccan aggttanaac taaaccnaac tttttnttta cagtcnaact tnatttatta    180

ttacnanagt caaaactttc aacaacggat ntnttggntn tngcatcnat gaanaacnca    240

ncnaaatncn atacgtaata tnaattgcan anattngtna atcatcgaat ctttnaacgc    300

ccnntgcncc ctttggtatt ccaaanggca ngcctgtttn ancgtcattt ntcccncnaa    360

cccccgggnt tggtgttnaa cnanacccna ggtttgtttg aaaaaattta acgtggaaac    420

ttattttaaa cgacttaggt ttatccnaaa acgcttattt tgctagggcc accacaattt    480

atttcaaact tgaccca                                                   497


<210> SEQ ID NO 33
<211> LENGTH: 496
<212> TYPE: DNA
<213> ORGANISM: Candida parapsilosis
<220> FEATURE:
<221> NAME/KEY: misc_feature
<222> LOCATION: (0)...(0)
<223> OTHER INFORMATION: n = a or c or g or t

<400> SEQUENCE: 33

ggaagtaaaa agtcggtaac aaggtttccg taggtgaacc tgcggaagga tcattacaga     60

atgaaaagtg cttaactgca ttttttctta cacatgtgtt tttctttttt tgaaaacttt    120

gctttggtag gccttctata tggggcctgc cagagattaa actcaaccaa attttattta    180

atgtcanccg attatttaat agtcaaaact ttcaacaacg gatctcttgg ttctcgcatc    240

gatgaagaac gcagcgaaat gcgataagta atatgaattg cagatattcg tgaatcatcg    300

aatctttgaa cgcncattgc gccctttggt attccaaagg gcatgcctgt ttgagcgtca    360

tttctcccnc aaaccctcgg gtttggtgtt gagcgatacg ctgggtttgc ttgaaagaaa    420

ggcggagtat aaactaatgg ataggttttt tccactcatt ggtacaaact ccaaaacttc    480

ttccaaattc gaccca                                                    496


<210> SEQ ID NO 34
<211> LENGTH: 595
<212> TYPE: DNA
<213> ORGANISM: Aspergillus flavus

<400> SEQUENCE: 34

tccgtaggtg aacctgcgga aggatcatta ccgagtgtag ggttcctagc gagcccaacc     60

tcccacccgt gtttactgta ccttagttgc ttcggcgggc ccgccattca tggccgccgg    120
```

-continued

```
gggctctcag ccccgggccc gcgcccgccg gagacaccac gaactctgtc tgatctagtg    180

aagtctgagt tgattgtatc gcaatcagtt aaaactttca acaatggatc tcttggttcc    240

ggcatcgatg aagaacgcag cgaaatgcga taactagtgt gaattgcaga attccgtgaa    300

tcatcgagtc tttgaacgca cattgcgccc cctggtattc cggggggcat gcctgtccga    360

gcgtcattgc tgcccatcaa gcacggcttg tgtgttgggt cgtcgtcccc tctccggggg    420

ggacgggccc caaaggcagc ggcggcaccg cgtccgatcc tcgagcgtat ggggctttgt    480

cacccgctct gtaggcccgg ccggcgcttg ccgaacgcaa atcaatcttt ttccaggttg    540

acctcggatc aggtagggat acccgctgaa cttaagcata tcaataagcg gagga         595
```

<210> SEQ ID NO 35
<211> LENGTH: 597
<212> TYPE: DNA
<213> ORGANISM: Aspergillus fumigatus

<400> SEQUENCE: 35

```
tccgtaggtg aacctgcgga aggatcatta ccgagtgagg gccctttggg tccaacctcc     60

cacccgtgtc tatcgtacct tgttgcttcg gcgggcccgc cgtttcgacg gccgccgggg    120

aggccttgcg cccccgggcc cgcgcccgcc gaagacccca acatgaacgc tgttctgaaa    180

gtatgcagtc tgagttgatt atcgtaatca gttaaaactt tcaacaacgg atctcttggt    240

tccggcatcg atgaagaacg cagcgaaatg cgataactaa tgtgaattgc agaattcagt    300

gaatcatcga gtctttgaac gcacattgcg ccccctggta ttccgggggg catgcctgtc    360

cgagcgtcat tgctgccctc aagcacggct tgtgtgttgg gcccccgtcc ccctctcccg    420

ggggacgggc ccgaaaggca gcggcggcac cgcgtccggt cctcgagcgt atggggcttt    480

gtcacctgct ctgtaggccc ggccggcgcc agccgacacc caactttatt tttctaaggt    540

tgacctcgga tcaggtaggg atacccgctg aacttaagca tatcaataag cggagga       597
```

<210> SEQ ID NO 36
<211> LENGTH: 565
<212> TYPE: DNA
<213> ORGANISM: Aspergillus nidulans

<400> SEQUENCE: 36

```
tccgtaggtg aacctgcgga aggatcatta ccgagtgcgg gctgcctccg ggcgcccaac     60

ctcccacccg tgactactaa cactgttgct tcggcgggga gccccccagg ggcgagccgc    120

cggggaccac tgaacttcat gcctgagagt gatgcagtct gagcctgaat acaaatcagt    180

caaaactttc aacaatggat ctcttggttc cggcatcgat gaagaacgca gcgaactgcg    240

ataagtaatg tgaattgcag aattcagtga atcatcgagt ctttgaacgc acattgcgcc    300

ccctggcatt ccgggggca tgcctgtccg agcgtcattg ctgccctcaa gcccggcttg    360

tgtgttgggt cgtcgtcccc cccgggggac gggcccgaaa ggcagcggcg gcaccgtgtc    420

cggtcctcga gcgtatgggg ctttgtcacc cgctcgatta gggccggccg ggcgccagcc    480

ggcgtctcca accttatttt tctcaggttg acctcggatc aggtagggat acccgctgaa    540

cttaagcata tcaataagcg gagga                                          565
```

<210> SEQ ID NO 37
<211> LENGTH: 599
<212> TYPE: DNA
<213> ORGANISM: Aspergillus niger

<400> SEQUENCE: 37

-continued

```
tccgtaggtg aacctgcgga aggatcatta ccgagtgcgg gtcctttggg cccaacctcc     60

catccgtgtc tattgtaccc tgttgcttcg gcgggcccgc cgcttgtcgg ccgccggggg    120

ggcgcctctg ccccccgggc ccgtgcccgc cggagacccc aacacgaaca ctgtctgaaa    180

gcgtgcagtc tgagttgatt gaatgcaatc agttaaaact ttcaacaatg gatctcttgg    240

ttccggcatc gatgaagaac gcagcgaaat gcgataacta atgtgaattg cagaattcag    300

tgaatcatcg agtctttgaa cgcacattgc gccccctggt attccggggg gcatgcctgt    360

ccgagcgtca ttgctgccct caagcccggc ttgtgtgttg ggtcgccgtc cccctctccg    420

gggggacggg cccgaaaggc agcggcggca ccgcgtccga tcctcgagcg tatggggctt    480

tgtcacatgc tctgtaggat tggccggcgc ctgccgacgt tttccaacca ttctttccag    540

gttgacctcg gatcaggtag ggatacccgc tgaacttaag catatcaata agcggagga     599
```

<210> SEQ ID NO 38
<211> LENGTH: 608
<212> TYPE: DNA
<213> ORGANISM: Aspergillus terreus

<400> SEQUENCE: 38

```
tccgtaggtg aacctgcgga aggatcatta ccgagtgcgg gtctttatgg cccaacctcc     60

cacccgtgac tattgtacct tgttgcttcg gcgggcccgc cagcgttgct ggccgccggg    120

gggcgactcg cccccgggcc cgtgcccgcc ggagacccca acatgaaccc tgttctgaaa    180

gcttgcagtc tgagtgtgat tctttgcaat cagttaaaac tttcaacaat ggatctcttg    240

gttccggcat cgatgaagaa cgcagcgaaa tgcgataact aatgtgaatt gcagaattca    300

gtgaatcatc gagtctttga acgcacattg cgccccctgg tattccgggg ggcatgcctg    360

tccgagcgtc attgctgccc tcaagcccgg cttgtgtgtt gggccctcgt cccccggctc    420

ccgggggacg ggcccgaaag gcagcggcgg caccgcgtcc ggtcctcgag cgtatggggc    480

ttcgtcttcc gctccgtagg cccggccggc gcccgccgac gcatttattt gcaacttgtt    540

tttttccagg ttgacctcgg atcaggtagg gatacccgct gaacttaagc atatcaataa    600

gcggagga                                                             608
```

<210> SEQ ID NO 39
<211> LENGTH: 569
<212> TYPE: DNA
<213> ORGANISM: Aspergillus ustus

<400> SEQUENCE: 39

```
tccgtaggtg aacctgcgga aggatcatta ccgagtgcag gtctgccccg ggcaggccta     60

acctcccacc cgtgaatacc tgaccaacgt tgcttcggcg gtgcgcccct ccgggggtag    120

ccgccggaga ccacaccgaa cctcctgtct ttagtgttgt ctgagcttga tagcaaacct    180

attaaaactt tcaacaatgg atctcttggt tccggcatcg atgaagaacg cagcgaactg    240

cgataagtaa tgtgaattgc agaattcagt gaatcatcga gtctttgaac gcacattgcg    300

ccccctggca ttccgggggg catgcctgtc cgagcgtcat tgctgccctt caagcccggc    360

ttgtgtgttg ggtcgtcgtc cctccggggg gacgggcccg aaaggcagcg gcggcaccgc    420

gtccggtcct cgagcgtatg ggctttgtc acccgctcga ttagggccgg ccgggcgcca    480

gccggcgtct ccaacctttt attttaccag gttgacctcg gatcaggtag ggatacccgc    540

tgaacttaag catatcaata agcggagga                                      569
```